(12) United States Patent
Al-Mayah

(10) Patent No.: US 10,206,575 B2
(45) Date of Patent: Feb. 19, 2019

(54) APPARATUS AND METHOD FOR USING INTERNAL INCLUSION FOR MECHANICAL CHARACTERIZATION OF SOFT MATERIALS

(71) Applicant: Adil Al-Mayah, Waterloo (CA)

(72) Inventor: Adil Al-Mayah, Waterloo (CA)

( * ) Notice: Subject to any disclaimer, the term of this patent is extended or adjusted under 35 U.S.C. 154(b) by 450 days.

(21) Appl. No.: 14/959,495

(22) Filed: Dec. 4, 2015

(65) Prior Publication Data

US 2017/0160175 A1 Jun. 8, 2017

(51) Int. Cl.
*A61B 5/00* (2006.01)
*G01L 5/00* (2006.01)
*G01N 3/12* (2006.01)
*G01N 33/38* (2006.01)

(52) U.S. Cl.
CPC .......... *A61B 5/0053* (2013.01); *A61B 5/6853* (2013.01); *G01L 5/00* (2013.01); *G01N 3/12* (2013.01); *G01N 33/383* (2013.01); *G01N 2203/0044* (2013.01); *G01N 2203/0089* (2013.01)

(58) Field of Classification Search
CPC ...... A61B 5/037; A61B 5/0053; A61M 25/10; A61M 25/10182
USPC ........................................ 600/561, 591, 587
See application file for complete search history.

(56) References Cited

U.S. PATENT DOCUMENTS

| | | | | |
|---|---|---|---|---|
| 3,448,739 A * | 6/1969 | Raible | ................... | A61M 25/10 600/435 |
| 5,048,532 A * | 9/1991 | Hickey | ................ | A61B 5/0215 600/485 |
| 5,135,488 A * | 8/1992 | Foote | ................ | A61M 25/1018 604/100.03 |
| 5,265,612 A | 11/1993 | Sarvazyan et al. | | |
| 5,951,497 A * | 9/1999 | Wallace | ................ | A61B 5/035 600/176 |
| 6,021,781 A * | 2/2000 | Thompson | ............. | A61B 5/036 128/898 |
| 6,063,045 A * | 5/2000 | Wax | ...................... | A61M 25/10 482/112 |
| 6,631,647 B2 | 10/2003 | Seale | | |
| 8,876,735 B2 | 11/2014 | Chuang et al. | | |

(Continued)

FOREIGN PATENT DOCUMENTS

WO 2013156415 A1 10/2013
WO 2014122011 A1 8/2014

OTHER PUBLICATIONS

Borisov, A.V. (2010), "Elastic analysis of multilayered thick-walled spheres under external load", Mechanika, No. 4 (84), pp. 28-32.

(Continued)

*Primary Examiner* — Max Hindenburg
(74) *Attorney, Agent, or Firm* — Bereskin & Parr LLP/ S.E.N.C.R.L., s.r.l.; Tony Orsi

(57) ABSTRACT

Various embodiments are described herein of methods and systems for measuring at least one mechanical characteristic of a soft material are provided according to the teachings herein. The embodiments described herein generally employ the use of a mechanical inclusion in the soft material, measuring at least one pressure and volume data point and applying a mechanical relation associated with the mechanical characteristic(s) to the measured data point(s) to determine the mechanical characteristic(s).

19 Claims, 9 Drawing Sheets

(56) References Cited

U.S. PATENT DOCUMENTS

| | | | |
|---|---|---|---|
| 8,886,334 B2 | 11/2014 | Ghaffari et al. | |
| 9,012,784 B2 | 4/2015 | Arora et al. | |
| 9,622,670 B2* | 4/2017 | Burnett | A61B 5/036 |
| 9,662,058 B2* | 5/2017 | Burnett | A61B 5/205 |
| 2014/0295538 A1 | 10/2014 | Franck et al. | |

OTHER PUBLICATIONS

Fung, Y.C. (1993) "Biomechanics: Mechanical Properties of Living Tissues", Springer-Verlag, New York, second edition, Chapter 7, Bioviscoelastic solids, pp. 242-320.
Gent, A. N.; and Lindley P. B. (1959), "Internal Rupture of Bonded Rubber Cylinders in Tension", Proceedings of the Royal Society A: Mathematical, Physical and Engineering Sciences , vol. 249, No. 1257, pp. 195-205.
Lim, Y. J.; Deo, D., Singh, T. P., Jones, D. B, De, S. (2009) "In situ measurement and modeling of biomechanical response of human cadaveric soft tissues for physics-based surgical simulation", Surgical endoscopy 23, pp. 1298-1307.
Misra, K., Ramesh, T., and Okamura A. M. (2008) "Modeling of tool tissue interactions for computer-based surgical simulation: A literature review", Presence-Teleoperators and Virtual Environments 17, pp. 463-491.
Muller, M., Gennisson, J. L., Detheux, T., Tanter, M., and Fink, M. (2009) "Quantitative viscoelasticity mapping of human liver using supersonic shear imaging: preliminary in vivo feasibility study", Ultrasound in Medicine and Biology 35, pp. 219-229.
Roylance, David (2001); "Engineering Viscoelasticity", http://ocw.mit.edu/courses/materials-science-and-engineering/3-11-mechanics-of-materials-fall-1999/modules/visco.pdf.
Martins, P. A. L. S., Natal Jorge, R. M., and Ferreira A. J. M. (2006). A Comparative Study of Several Material Models or Prediction of Hyperelastic Properties: Application to Silicone-Rubber and Soft Tissues. Strain 42: pp. 135-147.
Boyce, M. C. and Arruda, E. M. 2000. Constitutive Models of Rubber Elasticity: A Review. Rubber chemistry and technology 73: pp. 504-523.
Alterovitz, R., Pouliot, J., Taschereau, R., Hsu, I.C.J., and Goldberg, K. (2003) "Simulating needle insertion and radioactive seed implantation for prostate brachytherapy", Studies in Health Technology and Informatics Westwood et al.,editor, Medicine meets virtual reality 11 (MMVR11), pp. 19-25.
Arani A., Plewes, D., Krieger, A., and Chopra, R. (2011) "The Feasibility of Endorectal MR Elastography for Prostate Cancer Localization", Magnetic Resonance in Medicine 66, pp. 1649-1657.
Baba, M., Furuya, K., Bandou, H., Kasai, K., and Sadaoka, K. (2011) "Discrimination of individuals in a general population at high-risk for alcoholic and non-alcoholic fatty liver disease based on liver stiffness: A cross section study", BMC Gastroenterology 11, Article No. 70, 9 pages.
Bahn, M.M., Brennan, M.D., Bahn, R.S., Dean, D.S., Kugel, J.L., and Ehman, R.L. (2009) "The Development and application of magnetic resonance elastography of the normal and pathological thyroid gland in vivo", Journal of Magnetic Resonance Imaging 30, pp. 1151-1154.
Biswas, R., Patel, P., Park, D.W., Cichonski, T.J., Richards, M.S., Rubin, J.M., Hamilton, J., and Weitzel, W.F. (2010) "Venous elastography: validation of a novel high-resolution ultrasound method for measuring vein compliance using mite element analysis", Seminars in Dialysis 23, pp. 105-109.
Boyd, N.F., Lockwood, G.A., Byng, J.W., Tritchler, D.L., and Yaffe, M.J. (1998) "Mammographic densities and breast cancer risk", Cancer epidemiology, biomarkers and prevention 7, pp. 1133-1144.
Brisson, J., Morrison, A.S., Kopans, D.B., et al. (1984) "Height and weight, mammographic features of breast tissue, and breast cancer risk", American journal of epidemiology 119, pp. 371-381.
Brock, K.K., Dawson, L.A., Shame, M.B., Moseley, D.J., and Jaffray, D.A. (2006) "Feasibility of a novel deformable image registration technique to facilitate classification, targeting, and monitoring of tumor and normal tissue", International Journal of Radiation Oncology Biology Physics 64, pp. 1245-1254.
Bursa, J., and Zemanek, M. (2008) "Evaluation of biaxial tension tests of soft tissues", Studies in Health Technology and Informatics 133, pp. 45-55.
Butcher, D.T., Alliston, T., and Weaver, V.M. (2009) "A tense situation: forcing tumour progression", Cancer epidemiology, biomarkers and prevention 9, pp. 108-122.
Carter, F.J., Frank, T.G., Davies, P.J., McLean, D., and Cuschieri, A., (2001) "Measurement and modelling of the compliance of human and porcine organs", Medical Image Analysis 5, pp. 231-236.
Carter, T.J., Sermesant, M., Cash, D.M., Barratt, D.C., Tanner, C., and Hawkes, D.J. (2005) "Application of soft tissue modelling to image-guided surgery", Medical Engineering and Physics 27, pp. 893-909.
Carson, W.C., Gerling, G.J., Krupski, T.L., Kowalik, C.G., Harper, J.C., and Moskaluk, C.A. (2011) "Material aharacterization of ex vivo prostate tissue via spherical indentation in the clinic", Medical Engineering & Physics 33, pp. 302-309.
Castaneda, B., Hoyt, K., Westesson, K., An, L., Baxter, L., Joseph, J., Strang, J., Rubens, D., and Parker, K. (2009) "Performance of three-dimensional sonoelastography in prostate cancer detection: a comparison between ex vivo and in vivo experiments", Proc. IEEE Ultrason. Symp. (Sep. 20-23, 2009, Rome, Italy), pp. 519-522.
Cournane, S., Cannon, L., Browne, J.E., and Fagan, A.J. (2010) "Assessment of the accuracy of an ultrasound elastography liver scanning system using a PVA-cryogel phantom with optimal acoustic and mechanical properties", Physics in Medicine and Biology 55, pp. 5965-5983.
del Palomar, A.P., Calvo, B., Herrero, J., López, J., and Doblaré, M. (2008) "A finite element model to accurately predict real deformations of the breast", Medical engineering and physics 30, pp. 1089-1097.
Dighe, M., Kim, J., Luo, S., and Kim, Y. (2010) "Utility of the ultrasound elastographic systolic thyroid stiffness index in reducing fine-needle aspirations", Journal of Ultrasound in Medicine 29, pp. 565-574.
DiMaio S.P., and Salcudean S.E. (2005) "Interactive simulation of needle insertion models", IEEE Transactions on Bio-medical Engineering 52, pp. 1167-1179.
Gao, Z., Lister, K., and Desai, J.P. (2010) "Constitutive Modeling of Liver Tissue: Experiment and Theory", Annals of Biomedical Engineering 38, pp. 505-516.
Goksel, O., Salcudean, S.E., and DiMaio, S.P. (2006) "3D simulation of needle-tissue interaction with application to prostate brachytherapy", Journal of Image Guided Surgery 11, pp. 279-288.
Goss, B.C., McGee, K.P., Ehman, E.G., Manduca, A., and Ehman, R.L. (2006) "Magnetic resonance elastography of the lung: Technical feasibility", Magnetic Resonance in Medicine, 56, pp. 1060-1066.
Hajji, M.A., Wilson, T.A., and Lai-Fook, S.J. (1979) "Improved measurements of shear modulus and pleural membrane tension of the lung", Journal of Applied Physiology 47, pp. 175-181.
Hawkes, D.J., Penney, G., Atkinson, D., Barratt, D., Blackall, J., Carter, T., Crum, W.R., McClelland, J., Tanner, C., Tarte, S., White, M. (2007) "Motion and biomechanical models for image-guided interventions", Biomedical Imaging: From Nano to Macro, pp. 992-995.
Hoyt, K., Castaneda, B., Zhang, M., Nigwekar, P., di Sant'agnese, P.A., Joseph, J.V., Strang, J., Rubens, D.J., and Parker, K.J. (2008) "Tissue elasticity properties as biomarkers for prostate cancer", Cancer Biomarker 4, pp. 213-225.
Humphrey, J.D. (2003) "Continuum biomechanics of soft biological tissues", Proceedings of the Royal Society of London. Series A, Mathematical and physical sciences 459, pp. 3-46.
Jordan, P., Socrate, S., Zickler, T.E., and Howe R.D. (2009) "Constitutive modeling of porcine liver in indentation using 3D ultrasound imaging", Journal of the Mechanical Behavior of Biomedical Materials 2, pp. 192-201.
Kemper, J., Sinkus, R., Lorenzen, J., Nolte-Ernsting, C., Stork, A., and Adam, G. (2004) "MR elastography of the prostate: initial in-vivo application", Rofo 176, pp. 1094-1099.

(56) References Cited

OTHER PUBLICATIONS

Kerdok, A.E., Ottensmeyer, M.P., and Howe, R.D. (2006) "Effects of perfusion on the viscoelastic characteristics of liver", Journal of Biomechanics 39, pp. 2221-2231.

Krol, A., Unlu, M.Z., and Baum, K.G. (2006) "MRI/PET nonrigid breast-image registration using skin fiducial markers", Physica Medica 21, pp. 39-43.

Krouskop, T.A., Wheeler, T.M., Kallel. F., Garra, B.S., and Hall, T. (1998) "Elastic moduli of breast and prostate tissues under compression", Ultrasonic Imaging 20, pp. 260-274.

Mariappan, Y.K., Kolipaka, A., Manduca, A., Hubmayr, R.D., Ehman, R.L., Araoz, P., McGee, K.P. (2012) "magnetic resonance elastography of the lung parenchyma in an in situ porcine model with a non-invasive mechanical driver: Correlation of Shear Stiffness with Trans-respiratory system Pressures", Magnetic Resonance in Medicine 67, pp. 210-217.

McAnearney, S., Fedorov, A., Joldes, G., Hata, N., Tempany, C., Miller, K., and Wittek, A. (2011) "The effects of Young's Modulus on predicting prostate deformation for MRI-guided interventions", Computational Biomechanics for Medicine, Part1, pp. 39-49.

McGrath, D., Foltz, W., Al-Mayah, A., Niu, C., and Brock, K. (2011) "Quasi-Static Magnetic Resonance Elastography at 7 Tesla to Measure the effect of Pathology Fixation on Tissue Material Properties", Magnetic Resonance in Medicine (In press; Published online).

McKee, C.T., Last, J.A., Russell, P., and Murphy, C.J. (2011) "Indentation versus tensile measurements of Young's modulus for soft biological tissues", Tissue Engineering Part B: Reviews 17, pp. 155-164.

Miller, K., and Chinzei, K (2002) "Mechanical properties of brain tissue in tension", Journal of Biomechanics 35, pp. 483-490.

Naini, A.S., Patel, R.V., and Samani, A. (2011) "Measurement of Lung Hyperelastic Properties Using Inverse Finite Element Approach", IEEE Transactions on Biomedical Engineering 58, pp. 2852-2859.

Nava, A., Mazza, E., Furrer, M., Villiger, P., Reinhart, W.H. (2008) "In vivo mechanical characterization of human liver", Medical Image Analysis 12, pp. 203-216.

Oka, Y. I, Sakohara, S., Gotoh, T., Iizawa, T., Okamoto, K., and Hirofumi Doi, H. (2004) "Measurements of Mechanical Properties on a Swollen Hydrogel by a Tension Test Method", Polymer Journal 36, pp. 59-63.

Ophir, J., Céspedes, I., Ponnekanti, H., Yazdi, Y. And Li, X. (1991) "Elastography: a quantitative method for imaging the elasticity of biological tissues", Ultrasonic Imaging 13, pp. 111-134.

Perriñez, P.R., Kennedy, F.E., Van Houten, E.W., Weaver, J.B., and Paulsen, K.D. (2010) "Magnetic Resonance Poroelastography: An Algorithm for Estimating the Mechanical Properties of Fluid-Saturated Soft Tissues", IEEE Transaction on Medical Imaging 29, pp. 746-755.

Plewes, D.B., Bishop, J., Samani, A., and Sciarrefta, J. (2000) "Visualization and quantification of breast cancer biomechanical properties with magnetic resonance elastography", Physics in Medicine and Biology 45, pp. 1591-1610.

Ross K. A. and Scanlon M. G (1999) "Analysis of the elastic modulus of agar gel by indentation", J. Text. Stud. 30, pp. 17-27.

Ruiter, N.V., Stotzka, R., Muller, T.O., and Gemmeke, H. (2004) "Model-based registration of X-ray mammograms and MR images of the female breast", 2004 IEEE Nuclear Science Symposium Conference Record 5, pp. 3290-3294.

Salisbury, C.P., and Cronin D.S. (2009) "Mechanical Properties of Ballistic Gelatin at High Deformation Rates", Experimental Mechanics 49, pp. 829-840.

Samani, A., and Plewes, D.B. (2004) "A method to measure the hyperelastic parameters of ex vivo breast tissue samples", Physics in Medicine and Biology 49, pp. 4395-4405.

Samani, A., Bishop, J. and Plewes, D.B. (2001) "Biomechanical 3-D finite element modeling of the human breast using MRI data", IEEE Transactions on Medical Imaging 20, pp. 271-279.

Samani, A. and Plewes, D. (2007) "An inverse problem solution for measuring the elastic modulus of intact ex vivo breast tissue tumours", Physics in Medicine and Biology 52, pp. 1247-1260.

Venkatesh, S.K., Yin, M., Glockner, J.F., Takahashi, N., Araoz, P.A., Talwalkar, J.A., and Ehman, R.L. (2008) "MR Elastography of liver tumors: preliminary results", American Journal of Roentgenology 190, pp. 1534-1540.

Wang, J.H., Changchien, C.S., Hung, C.H., Eng, E L., Tung, W.C., Kee, K.M., Chen, C.H., Hu, T.H., Lee, C.M., and Lu, S.N. (2009) "FibroScan and ultrasonography in the prediction of hepatic fibrosis in patients with chronic viral hepatitis", Journal Gastroenterology 44, pp. 439-446.

Wojcinski, S., Farrokh, A., Weber, S., Thomas, A., Fischer, T., Slowinski, T., Schmidtand, W., and Degenhardt, F. (2010) "Multicenter study of ultrasound real-time tissue elastography in 779 cases for the assessment of breast lesions:improved diagnostic performance by combining the BI-RADS®—US classification system with sonoelastography", Ultraschall Med. 31, pp. 484-491.

Yaghjyan, L., Mahoney, M.C., Succop, P., Wanes, R., Buckholz, J., and Pinney, S.M. (2012) "Relationship between breast cancer risk factors and mammographic breast density in the Fernald Community Cohort", British Journal of Cancer 2012, pp. 1-8.

Yeh, W.C., Li, P.C., Jeng, Y.M., Hsu, H.C., Kuo, P.L., Li, M.L., Yang, P.M., and Lee, P.H (2002) "Elastic modulus measurements of human liver and correlation with pathology", Ultrasound in Medicine and Biology 28, pp. 467-474.

Zeng Y.J. Yager, D. and Fung, Y.C. (1987) "Measurement of the mechanical properties of the human lung tissue", Journal of Biomechanical Engineering 109, pp. 169-174.

Zhang Y., Qiu, Y., Goldgof, D.B., Sarkar, S., and Li, L. (2007) "3D Finite Element Modeling of Nonrigid Breast Deformation for Feature Registration in X-ray and MR Images", IEEE Workshop on Applications of Computer Vision, 6 pages.

Zhang, M., Nigwekar, P., Castaneda, B., Hoyt, K., Joseph, J.V., di Sant'Agnese, A., Messing, E.M., Strang, J.G., Rubens, D.J., Parker, K.J. (2008) "Quantitative characterization of viscoelastic properties of human prostate correlated with histology", Ultrasound in Medicine and Biology 34, pp. 1033-1042.

Huang, Y-P., Zheng, Y-P., "Measurement of Soft Tissue Elasticity in Vivo: Techniques and Applications", CRC Press, 2016, 226 pages.

Ophir, J., Alam, S.K., Garra, B.S. et al., "Elastography: Imaging the Elastic Properties of Soft Tissues with Ultrasound", J. Med Ultrasonics 2002: 29 p. 155-171.

Sahebjavaher, R.S., Baghani, Al, Honarvar, M. et al., "Transperineal Prostate Mr Elastography: Initital In Vivo Results", Magnetic Resonance in Medicine 69: 411-420 (2013).

\* cited by examiner

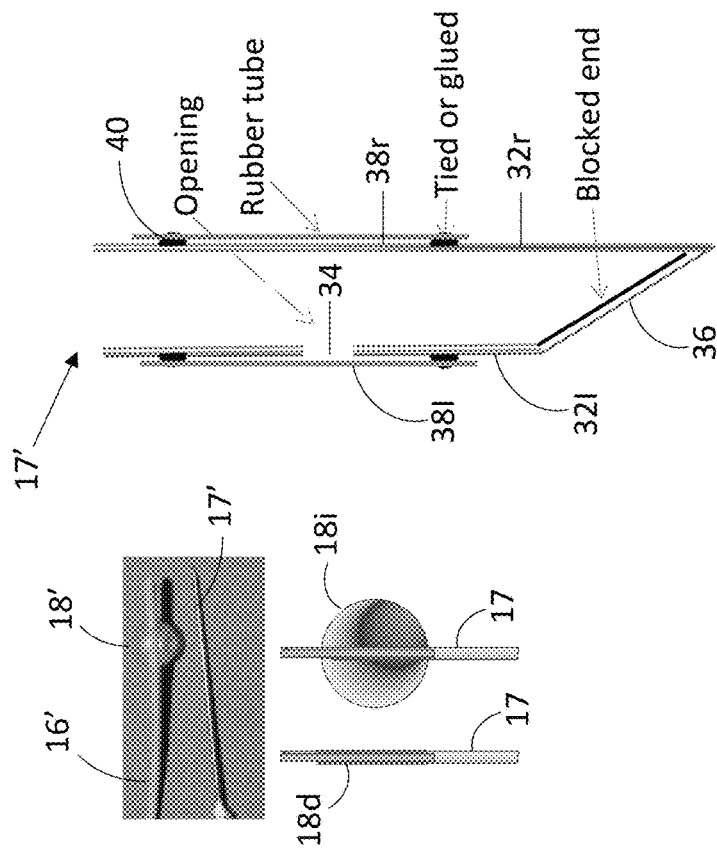
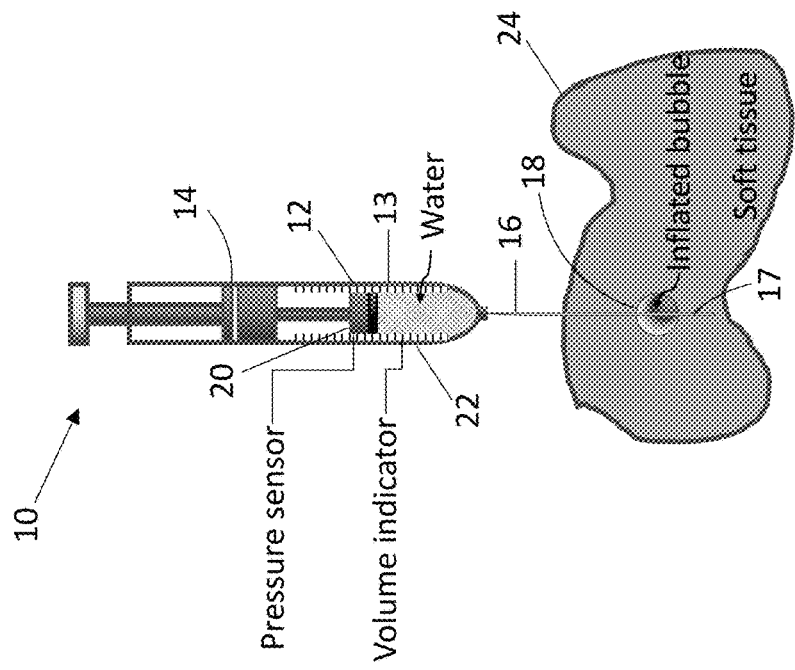
FIG. 1A
FIG. 1B
FIG. 1C

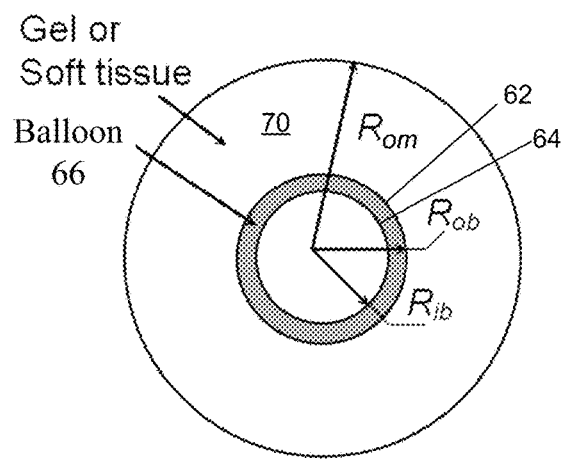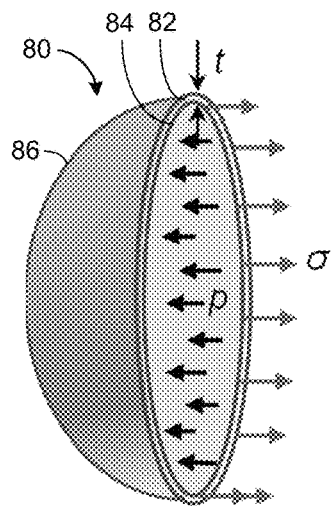
FIG. 4   FIG. 5
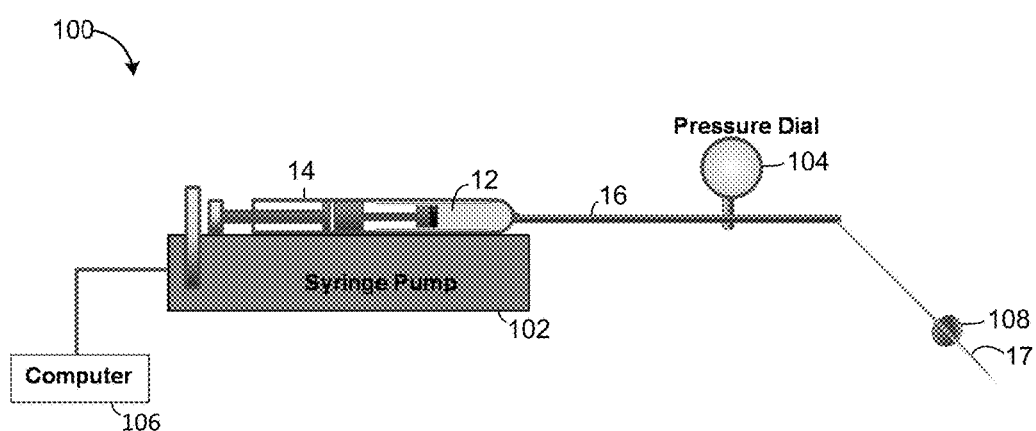
FIG. 6A

APPARATUS AND METHOD FOR USING INTERNAL INCLUSION FOR MECHANICAL CHARACTERIZATION OF SOFT MATERIALS

FIELD

The various embodiments described herein generally relate to an apparatus and method for determining at least one mechanical property of a soft material.

BACKGROUND

Soft material has been crucial in the advancement of a wide range of applications, spanning medical and engineering applications. Finding mechanical properties of these materials is useful for many applications (Misra et al., 2008). For example, in the medical field, computational biomechanical modeling has emerged as an integral part of the advancement of several medical applications, including image guided interventions, brachytherapy, diagnostics, robotic surgery, image segmentation, and surgery training simulation. Similarly, mechanical properties of widely used soft materials, such as gel, are used in various designs and applications including, but not limited to, the design of heart valves, breathing ventilators, drug delivery, tissue engineering, and wound dressing. Many other example applications for soft materials include, but are not limited to, surgery simulators for training and tools design, the design of bio-mimicking materials, the design of vehicles for crash safety, the design of heart valves, breathing ventilators, drug delivery, tissue engineering, wound dressing, and pharmaceuticals.

Finding accurate mechanical properties is still a challenge due to the complex, expensive, unrealistic, and time consuming conventional testing procedures. For example, current biomechanical modeling primarily relies on tissue parameters based on ex vivo samples, which requires cutting, preserving, gripping and mounting the sample. In addition, these ex vivo samples exhibit substantial differences from in vivo samples, due to the effect of blood circulation, temperature, and surrounding constraints for in vivo environments (Fung 1993, Miller 2005, Kerdok et al, 2006). Furthermore, most of the existing measurements are based on a limited number of samples with a large standard deviation due to variation in experimental procedures, such as time from tissue excision, storage medium, temperature, hydration, and experimental method, in addition to a wide variation of properties between individuals.

SUMMARY OF VARIOUS EMBODIMENTS

Various embodiments of methods and systems for measuring at least one mechanical characteristic of a soft material are provided according to the teachings herein. The embodiments described herein generally employ the use of a mechanical inclusion in the soft material, measuring at least one pressure and volume data point and applying a mechanical relation associated with the mechanical characteristic(s) to the measured data point(s) to determine the mechanical characteristic(s).

In a broad aspect, at least one embodiment described herein provides a measurement system for measuring at least one mechanical characteristic of a region of interest of a soft material, the measurement system comprising a balloon that is disposed within the region of interest of the soft material, the balloon being inflatable from a deflated position to at least one inflated position during use; a volume indicator to measure volume data for the balloon at each inflated position; a pressure indicator to measure pressure data for a corresponding pressure needed to inflate the balloon to each inflated position; and a mechanical characteristic analyzer that is configured to determine the at least one mechanical property by applying a mechanical relationship that corresponds to the at least one mechanical property to the measured volume and pressure data.

In at least some embodiments, the measurement system further comprises a fluid reservoir for containing a fluid that is used to inflate the balloon; a conduit that is coupled to the fluid reservoir and the balloon; and an actuator that is coupled to the fluid reservoir to apply a force to drive the fluid from the fluid reservoir to the balloon via the conduit to inflate the balloon during use.

In at least some embodiments, the conduit comprises at least one aperture that is in fluid communication with the balloon and the balloon is attached and has edges sealed circumferentially around the conduit using one of biocompatible cyanoacrylate, a glue, a bonding agent or a welding agent.

In at least some embodiments, the fluid comprises a liquid or a gas.

In at least some embodiments, the fluid comprises distilled water.

In at least some embodiments, the measurement system further comprising tubing to couple the conduit with the fluid reservoir, the fluid reservoir is a syringe and the conduit is a needle.

In at least some embodiments, the actuator comprises a syringe pump and the pressure indicator is a pressure sensor.

In at least some embodiments, the soft material comprises organic tissue and the needle comprises a 19 G, 20 G, 22 G or 26 G needle.

In at least some embodiments, the soft material comprises organic tissue and the balloon has a thickness that ranges from 0.02 to 0.05 mm and inflated diameters for different inflation positions including 3, 5 and 10 mm.

In at least some embodiments, the soft material comprises one of tissue, asphalt matrix, and non-hardened concrete.

In at least some embodiments, the mechanical relationship comprises a pressure-volume relationship from which the at least one mechanical characteristic is derived.

In at least some embodiments, the mechanical relationship comprises stress-stretch and stress-strain relationship.

In at least some embodiments, the soft material comprises a rubber-like material and the mechanical relationship comprises a neo-Hookean strain energy function.

In at least some embodiments, the mechanical relationship relates a modulus of elasticity of the soft material to the volume and pressure data.

In another broad aspect, at least one embodiment described herein provides a method of measuring at least one mechanical property of a region of interest of a soft material, the method comprising inserting a balloon in a deflated position within the region of interest; inflating the balloon to at least one inflated position; measuring volume and pressure data comprising a volume of the balloon at each inflated position and a corresponding pressure used to inflate the balloon to each inflated position; and determining the at least one mechanical property by applying a mechanical relationship that corresponds to the at least one mechanical property to the measured volume and pressure data.

In at least some embodiments, the method further comprises inserting a fluid into the balloon to inflate the balloon.

In at least some embodiments, the method further comprises inserting a gas or a liquid into the balloon to inflate the balloon.

In at least some embodiments, a pump is used to insert the fluid into the balloon and the measured volume is obtained from a flow rate of the pump.

In at least some embodiments, the determining act comprises using comprises a pressure-volume relationship, a stress-stretch relationship, a stress-strain relationship or a modulus of elasticity as the mechanical relationship.

In at least some embodiments, the soft material comprises a rubber-like material and the determining act comprising using a neo-Hookean strain energy function as the mechanical relationship.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described.

FIG. 1A is a general schematic diagram for an example embodiment of an apparatus for measuring at least one mechanical characteristic of a soft material in accordance with the teachings herein.

FIG. 1B shows how a deflated balloon can inflate and expand to a spherical balloon by injection of a fluid, such as water, for example.

FIG. 1C shows a magnified view of an example embodiment of a portion of the apparatus of FIG. 1A to show how fluid can be provided to the inflatable balloon of FIG. 1B.

FIG. 4 is a cross-sectional view of a balloon under internal pressure after insertion inside a soft material.

FIG. 5 is a cross-sectional view of a thin balloon under internal pressure.

FIG. 6A is a block diagram of another example embodiment of an apparatus for measuring soft tissue parameters in accordance with the teachings herein.

Figure 2:
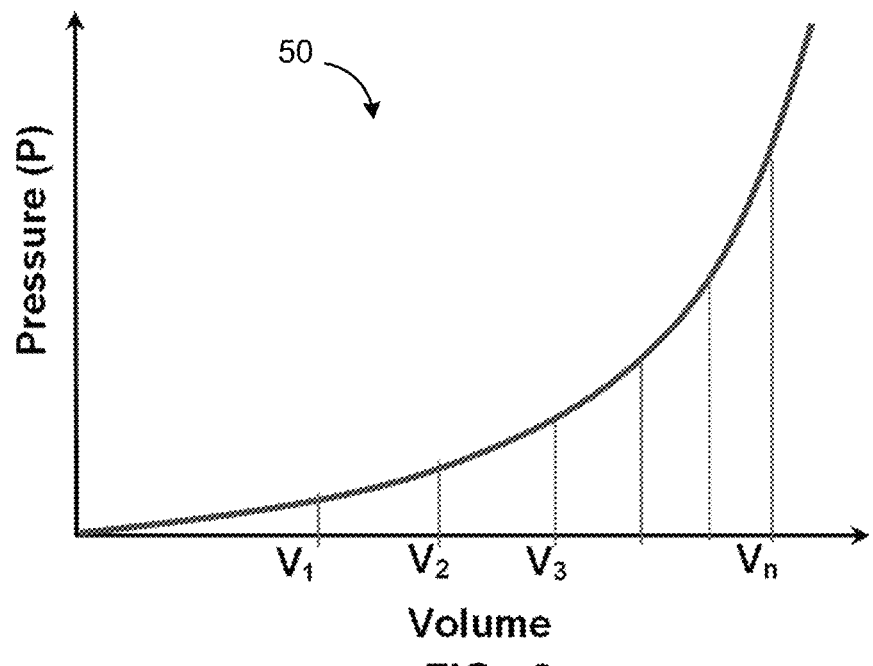
FIG. 2 shows an example plot of the pressure-volume relationship for an inflatable balloon inside a soft material.

Further aspects and features of the embodiments described herein will appear from the following description taken together with the accompanying drawings.

DETAILED DESCRIPTION OF THE EMBODIMENTS

Various apparatuses or processes will be described below to provide an example of at least one embodiment of the claimed subject matter. No embodiment described below limits any claimed subject matter and any claimed subject matter may cover processes, apparatuses or systems that differ from those described below. The claimed subject matter is not limited to apparatuses, processes or systems having all of the features of any one apparatus, process or system described below or to features common to multiple or all of the apparatuses, or processes or systems described below. It is possible that an apparatus, process or system described below is not an embodiment of any claimed subject matter. Any subject matter that is disclosed in an apparatus, process or system described below that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical or electrical connotation. For example, as used herein, the terms coupled or coupling can indicate that two elements or devices can be directly connected to one another or connected to one another through one or more intermediate elements or devices via an electrical element or electrical signal (either wired or wireless) or a mechanical element, such as, tubing or pipes, depending on the particular context.

It should be noted that terms of degree such as "substantially", "about" and "approximately" as used herein mean a reasonable amount of deviation of the modified term such that the end result is not significantly changed. These terms of degree may be construed as including a certain deviation of the modified term if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made if the end result is not significantly changed.

Also as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

Described herein are various example embodiments for a method and apparatus for measuring mechanical properties for a wide range of soft tissues and soft materials such as, but not limited to, tissues of liver, lung, breast (glandular and fat tissues), prostate, brain, parotid glands, kidney, muscles, and pancreas, in addition to hydrogel, and ballistic gel, for example. The technique can also be used in testing the compliance of blood vessels and bronchial tree. At least some of the various embodiments of the method and apparatus described in accordance with the teachings herein may be implemented such that they are efficient, cost effective, easy to use, and minimally invasive for in-vivo tissues. Furthermore, since the measurement methods described herein allow for measuring individual specific measurements, in some cases, rather than relying on an average of measurements across a group of materials that may have a wide variation in properties (as in the prior art), then the measurement methods herein reduce measurement variability.

The applicant's teachings herein generally involve the measured expansion of a small spherical balloon bubble (e.g. inclusion) inside a targeted soft material (e.g. surrounding material) such as, but not limited to tissue, for example. The expansion resistance imposed by the surrounding media around the balloon may be captured in the form of a pressure-volume relationship where stiffer materials exhibit a higher resistance to balloon expansion (i.e. a higher pressure is needed to inflate the balloon to a specific volume). The pressure-volume relationship can be translated into various mechanical relationships to determine at least one of the mechanical properties/characteristics of the surrounding media. For example, in some cases, the full stress-strain curve is used to characterize the soft material (i.e. multiple stress-strain points are needed which means multiple volume and pressure data points are obtained). However, in other cases, only one stress-strain point may need to be measured as the slope of the line between this specific point and the zero-zero point may be the mechanical characteristic which is being characterized (e.g. this slope represents the modulus of elasticity). The pressure-volume data and stress-strain relationship can be used to calculate other mechanical properties including, but not limited to, the bulk modulus (i.e. ratio of pressure to volume change), shear modulus, material resilience (e.g. the material's ability to absorb energy within the elastic deformation range), and viscoelastic properties (e.g. time dependent parameters such creep and relaxation parameters), for example.

In another aspect, at least one of the example embodiments of the method and apparatus described in accordance with the teachings herein can be used a stand-alone tool or can be integrated with other devices depending on the particular application. For example, an apparatus in accordance with the teachings herein can be integrated into a biopsy needle with multiple compartments, enabling measurement of the mechanical properties of the media surrounding the biopsy needle while collecting biological samples. Hence, in this example, no additional invasive procedure is required.

At least one of the various embodiments of the method and apparatus decreased in accordance with the teachings herein have been tested and validated in some gels and ex vivo liver tissues, and have also been further assessed by using numerical finite element modeling as will be discussed with regards to FIGS. 6A-9C.

Referring now to FIG. 1A, shown therein is a general schematic diagram for an example embodiment of a measurement apparatus 10 for measuring at least one mechanical characteristic of a soft material in accordance with the teachings herein. The measurement apparatus 10 comprises a fluid reservoir 12, an actuator 14, a conduit 16, a balloon 18, a pressure indicator 20 and a volume indicator 22. A proximal end of the conduit 16 is coupled to the fluid reservoir 12 and, a distal end 17 of the conduit 16 is embedded in the soft material 24 for which at least one mechanical characteristic is being measured. The balloon 18 is disposed near the distal end 17 of the conduit 18 and is shown in an inflated position. It should be noted that there may be different inflated positions in which the balloon 18 is inflated to a different degree (i.e. has a different volume) up to a maximum inflated position (i.e. maximum inflated position allowed by the size of the balloon 18 and the strength of the balloon material). Furthermore, the balloon 18 may deviate a bit from a perfect sphere as this has little effect on the measurement results (see FIG. 9). In other embodiments, the balloon 18 can be located at a different location on the conduit 16. However, in cases where the conduit 16 is a needle, to avoid patient discomfort, the balloon 18 may be inserted as deep as is needed which means that the balloon 18 is typically situated near the tip of the needle.

When the conduit 16 and the balloon 18 are inserted into a region of interest of the soft material 24 where the one or more mechanical characteristics are to be determined, the balloon 18 is in the deflated position. The fluid reservoir 12 contains a fluid 13 which is then injected or inserted into the conduit 16 due to pressure from a force provided by the actuator 14. At the region of the conduit 16 where the balloon 18 is located there are apertures connecting the interior of the conduit 16 with the interior of the balloon 18 to provide an efficient supply of the fluid 13 to the balloon 18 when the actuator 14 is actuated. The distal end of the conduit 16 is sealed so that the fluid 13 is supplied to the balloon 18 from the fluid reservoir 13 through the side opening 34 only. Therefore, when the fluid 13 is injected into the conduit 16, the fluid 13 will begin to fill (e.g. inflate) the balloon 18 so that the balloon 18 transitions from a deflated position to one of the inflated positions.

When the fluid 13 is injected into the balloon 18, the pressure indicator 20 and the volume indicator 22 are used to measure the pressure that is used to inject a certain volume of the fluid into the balloon 18. The measured pressure and volume data may then be used to determine one or more mechanical characteristics for the soft material 24. It should be noted that the pressure indicator 20 can be located at different locations such as on top of the syringe or at a location near the plunger (i.e. actuator 14).

In the example embodiment shown in FIGS. 1A-1C, the fluid reservoir 12 and actuator 14 may be implemented using a syringe with a plunger, respectively. In an alternative embodiment, an inflation device such as that used in angioplasty may be used instead of the syringe and plunger. The conduit 16 may be provided by a needle and the spherical balloon 18 (which may also be referred to as a bubble) is provided by a medical balloon. The medical balloon is attached to the external surface of the needle near to its sharp end. An implementation of the balloon is shown in FIG. 1B where the size of the balloon 18' is compared to a regular 20 G (gage) needle 17' having a 0.908 mm diameter. Different needle sizes may be used including, but not limited to, 19 G, 20 G, 22 G (having a 0.7176 mm diameter) and 26 G (having a 0.4636 mm diameter) depending on the applications (i.e. the geometry of the media that surrounds the needle 17 and the balloon 18.

In addition, different balloon sizes and wall thickness for the balloons can be used again depending on the application and the surrounding media. For example, balloons having a wall thickness that ranges from 0.02 to 0.05 mm can be used with an inflated diameter of 10.0, 5.0 and 3.0 mm (a 10 mm diameter has been used in the data shown herein). The deflated balloon is mounted on the needle with side holes 34 to provide an efficient supply of fluid to the balloon 18'. The bottom left panel of FIG. 1B shows the deflated balloon position 18d. FIG. 1C is a magnified view of the distal end of the needle showing how fluid can be provided to the balloon 18' via the conduit 17'. The conduit 17' has walls (two of which are shown as side walls 32r and 32l), a blocked or sealed end wall 36 and an aperture or hole 34 in the side wall 32l. In other embodiments, there can be additional apertures that are on opposite side walls at the same vertical height or at different vertical heights. Additional apertures may be added as long as the integrity of the conduit 17' is preserved. The balloon 18' has side walls (two of which are shown as side walls 38r' and 38l'. The side walls of the balloon 18' may be made of rubber tubing or another suitable material. The side walls of the balloon 18' may be attached to the side walls of the conduit 17' using any suitable attachment material that also provides a seal, such as, but not limited to, glue, thermal bonding (using heated die with air) or laser bonding, for example, at various connection points 40 (only one of which is labelled for simplicity). The sealed end wall 36 of the needle limits the fluid supply to the balloon only through the side hole 34. As the needle with the deflated balloon 18' is inserted at a specific depth inside the soft material 24, the balloon 18' is inflated to an inflated balloon position 18i (see the bottom right panel in FIG. 1B) by injecting fluid into it via the conduit 17' and the hole 34 while pressure and volume are measured. The balloon will be deflated before retracting the needle.

It should be noted that although the balloon 18' can be inserted at any depth allowed by the length of the conduit 17, in order to obtain accurate measurements, the minimum depth may be at least the maximum radius of the balloon 18' when in the maximum inflated position.

It should also be noted that any fluid or gas may be used as the fluid 13 such as, but not limited to, water and normal saline, for example. In particular, distilled water may be used for its incompressible nature, safety, and availability).

Furthermore, while the soft material 24 in this example is soft tissue, which may be in a living or non-living organism such as a person or an animal, for example, and the soft material 24 may be referred to as organic material. The apparatus 10 may be used in vivo with a living organism or ex vivo using a tissue sample. The soft tissue may be an organ, such as, but not limited to the liver, the lung, the heart, the kidney, the breast (fat and glandular tissues), prostate, the brain, and the pancreas, for example, or other body parts such as a particular muscle, soft cartilage, blood vessels, and the bronchial tube, for example. While experimental data has been obtained and analyzed for livers, these other types of tissues may be analyzed in a similar manner since they comprise material which is soft and can be perturbed by a variable inclusion, such as an inflatable balloon. It should be noted that the soft material 24 can also be a variety of non-living materials used in other applications including, but not limited to, hydrogel, ballistic gel, rubber like silicon, asphalt mix, and non-hardened concrete (e.g. concrete paste during casting), for example.

Measurements

The measurement methods described in accordance with the teachings herein involve recording data comprising volume measurements of the balloon 18 as it inflates and the corresponding pressure that is required to inflate the balloon 18. Referring now to FIG. 2, shown therein is an example plot 50 of the general relationship between applied pressure and measured volume for a fluid that is supplied to the balloon 18 using different volume intervals ranging from $V_1$ to $V_n$. Although, this pressure-volume relationship may be enough to predict at least one of the mechanical properties of a soft material which is experiencing the balloon inclusion, depending on the particular application, it may be used as a first step for a more detailed analysis of the mechanical properties of soft materials. For example, the pressure-volume relationship can be translated into different parameters using various relationships including, but not limited to, the stress-stretch, and the stress-strain relationships that represent the source to calculate other mechanical properties including, but not limited to, the bulk modulus (ratio of pressure to volume change), shear modulus, material resilience (a material's ability to absorb energy within elastic deformation range), and viscoelastic properties (time dependent parameters such creep and relaxation parameters). Some examples of using a pressure-volume relationship are illustrated with respect to equations 1 to 10.

Depending on the information used to measure one or more mechanical properties of the soft material, the measurement procedure can be classified into two categories: general stress-deformation relationship and simplified to measure the modulus of elasticity only. Following the general stress-deformation relationship procedure, the mechanics of the balloon alone (e.g. in air) before its insertion in the soft material medium can be determined. However, this may be eliminated by using very thin (e.g. <0.1 mm thickness) and/or very soft balloon material to minimize the contribution of the pressure within the balloon (e.g. the balloon) on restraining the expansion of the tested material (i.e. there is no need to characterize the balloon). This results in a very straight forward and fast reading of volume and corresponding pressure of the tested soft material.

It should be noted that although some analysis methods are presented in accordance with the teachings herein, in other embodiments other analytical methods may be used for different materials and/or different accuracies. For example, many strain energy functions, including, but not limited, to neo-Hookean, Mooney-Rivlin, polynomial Rivlin, Yeoh, Arruda and Boyce, and Ogden functions, may be available for measuring at least one mechanical property of rubber-like material. An example presented herein is the neo-Hookean's function.

Simplified Method
Incompressible or Nearly Incompressible and Nonlinear Elastic Materials Most soft materials are classified within the incompressible and nonlinear elastic material category including, but not limited to, gel and soft tissues. For incompressible or nearly incompressible materials (e.g. Poisson's ratio is around 0.5) and non-linear elastic (i.e. hyperelastic) materials, the mechanical properties are characterized according to a form of energy (W). Different energy functions have been proposed in the past that are based on the stress-stretching ratio relationship (Martins et al. 2006, Boyce and Arruda 2000). This stress-stretching relationship can be established using the pressure-volume data measured using the current technique. For example, the neo-Hookean's energy function is characterized by the following relationship (Gent and Lindley 1959):

$$W = \frac{E}{6}(\lambda_1^2 + \lambda_2^2 + \lambda_3^2 - 3) \tag{1}$$

where $\lambda_1$, $\lambda_2$, and $\lambda_3$ are the principal stretch ratios, and E is the modulus of elasticity.

For a spherical inclusion under internal pressure (P), the following relationship may be applied:

$$P = \frac{E}{6}\left(5 - \frac{4}{\lambda_0} - \frac{1}{\lambda_0^4}\right) \tag{2}$$

where $\lambda_0$ is the ratio of the deformed (e.g. inflated) inclusion radius to the undeformed (e.g. deflated) radius. According to this equation, if the spherical inclusion is inflated from a very small radius, the pressure may be approximated to be P=5E/6 which provides an easy way to predict the modulus of elasticity of the soft material using the balloon-based measurement methodology described in accordance with the teachings herein by measuring the pressure P at the a specified volume and solving for the modulus of elasticity E.

Compressible and Linear Elastic Materials

Figure 3:
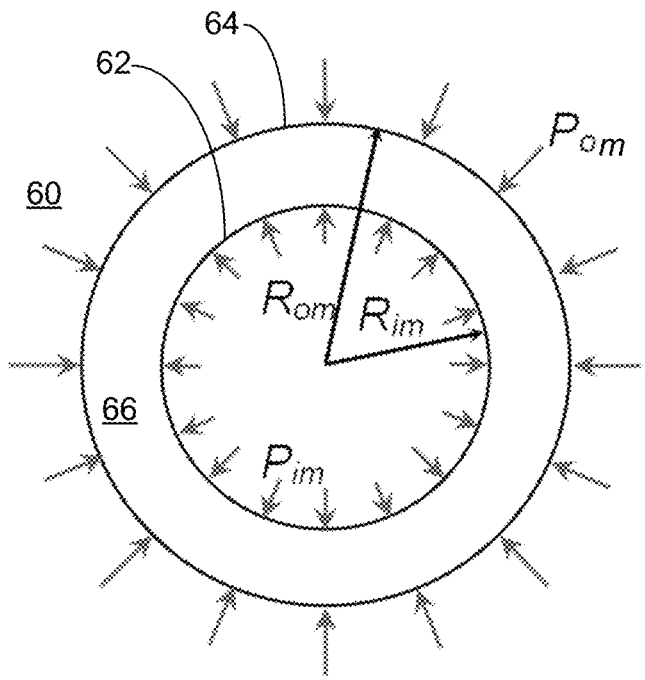
FIG. 3 is a cross-sectional view of a thick sphere under internal and external pressure.

In this case, the material 66 surrounding the balloon 18 may be considered as a hollow external thick wall sphere (R/t<10) and treated as isotropic material. In the general formulation of a thick wall sphere, the analysis may be based on the formulation of a sphere under internal ($P_{im}$) and external ($P_{om}$) pressures (see FIG. 3) (Borisov in 2010) to calculate the radial ($\sigma_{rr}$) and angular stresses (in a sphere, the angular stresses are equal i.e. $\sigma_{\theta\theta}=\sigma_{\varphi\varphi}$), as illustrated in the following equations:

$$\sigma_{rr} = \frac{1}{R_{om}^3 - R_{im}^3}\left(P_{im}R_{im}^3 - P_{om}R_{om}^3 - \frac{R_{om}^3 R_{im}^3}{r^3}(P_{im} - P_{om})\right) \tag{3}$$

$$\sigma_{\theta\theta} = \sigma_{\varphi\varphi} = \frac{1}{R_{om}^3 - R_{im}^3}\left(P_{im}R_{im}^3 - P_{om}R_{om}^3 + \frac{R_{om}^3 R_{im}^3}{2r^3}(P_{im} - P_{om})\right) \tag{4}$$

Similarly, radial ($\varepsilon_{rr}$) and angular strains ($\varepsilon_{\theta\theta}=\varepsilon_{\varphi\varphi}$) can be calculated using the following equations:

$$\varepsilon_{rr} = \frac{P_{im}R_{im}^3 - P_{om}R_{om}^3}{R_{om}^3 - R_{im}^3}\left(\frac{1-2v}{E}\right) - \frac{1}{r^3}\left(\frac{R_{om}^3 R_{im}^3(P_{im} - P_{om})}{R_{om}^3 - R_{im}^3}\right)\left(\frac{1+v}{E}\right) \tag{5}$$

$$\varepsilon_{\theta\theta} = \tag{6}$$

$$\varepsilon_{\varphi\varphi} = \frac{P_{im}R_{im}^3 - P_{om}R_{om}^3}{R_{om}^3 - R_{im}^3}\left(\frac{1-2v}{E}\right) + \frac{1}{r^3}\left(\frac{R_{om}^3 R_{im}^3(P_{im} - P_{om})}{R_{om}^3 - R_{im}^3}\right)\left(\frac{1+v}{2E}\right)$$

where v and E are the Poisson's ratio and modulus of elasticity of the material 66, respectively; r is the radial coordinate of any point inside the thick sphere wall 66 (the wall of the investigated soft material); $R_{im}$ and $R_{om}$ are internal and external radii of the material 66, respectively; and $P_{im}$ and $P_{om}$ are internal and external pressures applied on the material 66, respectively.

Referring now to FIG. 4 in which the balloon is located within a soft material 70, at r=$R_{om}$, $P_{om}$=0, the free external surface of the soft material 70 is not subjected to any stress. Also, the internal radius of the soft material 70 represents the external radius of the balloon 66 ($R_{im}$=$R_{ob}$) however, when the balloon 66 is thin ($R_{ib}$=$R_{ob}$) (as shown in FIG. 4 when the soft material is gel or soft tissue 70). In addition, the internal pressure on the soft material 70 represents the external pressure on the balloon ($P_{im}$=$P_{ob}$), and when the balloon is thin and soft ($P_{ob}$=$P_{ib}$=P) equations 3 and 4, for example, may be simplified to equations 7 and 8 (similar simplifications can be applied to equations 5 and 6).

$$\sigma_{rr} = \frac{PR_{im}^3}{R_{om}^3 - R_{im}^3}\left(1 - \frac{R_{om}^3}{r^3}\right) \tag{7}$$

$$\sigma_{\theta\theta} = \sigma_{\varphi\varphi} = \frac{PR_{im}^3}{R_{om}^3 - R_{im}^3}\left(1 + \frac{R_{im}^3}{2r^3}\right) \tag{8}$$

When the balloon is inserted in an infinite elastic medium (i.e. $R_{om}=\infty$), equations 3 and 4, for example, can be simplified further to equations 9 and 10.

$$\sigma_{rr} = -\left(P_{om} + \left(\frac{R_{im}}{r}\right)^3 (P_{im} - P_{om})\right) \tag{9}$$

$$\sigma_{\theta\theta} = \sigma_{\varphi\varphi} = -\left(P_{om} - \frac{1}{2}\left(\frac{R_{im}}{r}\right)^3 (P_{im} - P_{om})\right) \tag{10}$$

At this stage, it was observed in the preliminary studies on the applicant's measurement technique that the deformation induced by the balloon will be absorbed within a limited region around the rubber balloon. This finding and the assumption of an infinite medium (i.e. an outer radius is not needed) are of a practical significance where the outer radius is not known (as is the case with irregular organs or some soft material samples).

Balloon Characterization:

If needed, the behaviour of the balloon can be characterized via a model, and experimental investigation. Although any fluid can be used in this measurement method, distilled water is selected for its incompressible nature, safety, and availability. It should be noted that this characterization can be eliminated when a thin (e.g. <0.1 mm thickness) and/or soft (e.g. 5 times softer than tested materials) balloon is used, as is the case herein. Furthermore, the relatively minor contribution of the balloon on resisting the applied stress can be satisfactory eliminated by subtracting the difference between the pressure-volume plot for the balloon alone (in air and before its insertion into the soft material) and the pressure-volume plot for the balloon within the soft materials. Alternatively, a mathematical model may be used for general purpose analysis.

Modeling of the Balloon

There are two approaches that may be used to analyze the balloon: a linear elastic approach, and a nonlinear elastic approach. In the linear elastic approach, the modulus of elasticity may be used. In the nonlinear elastic approach, the pressure-volume or the pressure-stretch (λ) relationship may be used to establish the energy function (W). The linear elastic approach is explained below. The nonlinear elastic approach is similar to that related to the soft materials explained previously in the simplified method, except a thin layer assumption is applied for the balloon. The relationship between the volume change of the balloon (ΔV) and the strain (ε) is of practical use with the measurement apparatus 10 when using a syringe attached to a needle, as the volume change may be measured using numerical volume markings on the syringe (these numerical markings act as the volume indicator 22). Based on the volume equation of a sphere with a radius ($R_i$) at a specific interval (i), $V_i = 4/3\pi R_i^3$, and the increased volume ($V_{i+1}$) as more liquid is supplied to the bubble, $V_{i+1} = V_i + \Delta V = 4/3\pi (R_i + R_i \varepsilon)^3$, the volumetric strain can be determined as shown in equation 11.

$$\frac{\Delta V}{V} = 3\varepsilon + 3\varepsilon^2 + \varepsilon^3 \quad (11)$$

In this case, the volumes at the different intervals $V_i$ and $V_{i+1}$ and the corresponding change in volume ΔV can be measured and then equation 11 may be solved for the strain (ε). An understanding of the relationship between the strain and the applied pressure may then be used to characterize the balloon's deformation response to applied stress (σ). To find the relationship between the pressure and the strain, the balloon may be treated as a thin shell sphere having a wall thickness t under internal pressure because of the high ratio R/t>>10 where R is the radius, as shown in FIG. 5. As illustrated previously, there are three principal stresses of such a system: angular stresses ($\sigma_{\theta\theta} = \sigma_{\varphi\varphi}$), and radial stress ($\sigma_{rr}$). Although, the radial stress $\sigma_{rr}$ is small for thin structures and can be ignored, an average value over the thickness of the sphere shell (external pressure is zero in this case) of $\bar{e}_{rr} = \frac{1}{2}P$ may be used. The angular stresses ($\sigma_{\theta\theta} = \sigma_{\varphi\varphi}$) are constant and equal in all directions for spherical shell analysis. Therefore, equation 12 and 13 can be derived using the force equilibrium of the cross section shown in FIG. 5:

$$\varepsilon = \frac{PR}{2tE}(1-v) \quad (12)$$

$$\sigma_{\theta\theta} = \sigma_{\varphi\varphi} = \frac{PR}{2t} \quad (13)$$

where R and t are the radius and thickness of the sphere, respectively, E and v are the modulus of elasticity and Poisson's ratio, respectively, of the material used for the balloon (e.g. rubber) respectively, and P is the applied pressure. Therefore, the modulus of elasticity E can may be calculated determined using strain and pressure at a specific point of the P-V plot.

It should be noted that viscoelastic (e.g. time dependent) material properties may also be determined using at least one of the measurement techniques described herein by keeping the balloon inflated under a constant pressure (or a constant volume) for a period of time. To facilitate the measurement process, a constant bubble balloon volume can be created by injecting a constant amount of fluid into the balloon. This can be repeated for different pressure and volume data points when nonlinear material characterization is required, as shown in FIG. 2. Many types of viscoelastic relationships, such as Maxwell, Kelvin-Voigt, and standard linear solid, may be used as described by Roylance (2001), which is hereby incorporated by reference.

Results

Referring now to FIG. 6A, shown therein is a block diagram of an example embodiment of a prototype system 100 for measuring soft tissue parameters in accordance with the teachings herein. The system 100 comprises a syringe pump 102, a pressure dial gage 104 and a computer 106 along with the actuator 14, the fluid reservoir 12, the conduit 16 and a balloon 108 disposed near the end of the conduit 16. The computer 106 is a computing device that receives the measurement data and determines at least one mechanical property of the soft material that the balloon 108 was inserted within and then inflated. The computer 106 may be used to more accurately monitor the applied pressure with time and volume of the inflated balloon 108 as it is filled with fluid and inflated is known from the flow rate of the syringe pump and is correlated with time. The syringe pump 102 controls the movement of the actuator 14 to provide a specific flow rate for the fluid to the balloon 108 as compared to using a syringe that has a plunger that is manually actuated. The pressure dial gage 104 is optional but may be included and used as a second measure to monitor the pressure.

Figure 6B:
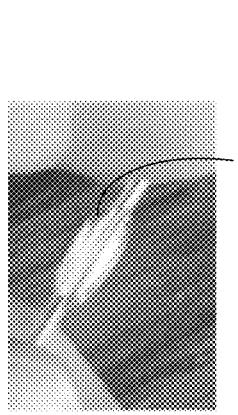
FIG. 6B-6F show portions of an experimental setup for the apparatus of FIG. 6A including an inflatable balloon (FIG. 6B), a catheter arrangement including a pressure sensor (FIG. 6C), a tube connection assembly (FIG. 6D), an electrical circuit (FIG. 6E) for connecting the pressure sensor to a computer, and an example embodiment of the computer (FIG. 6F).
Figure 6C:
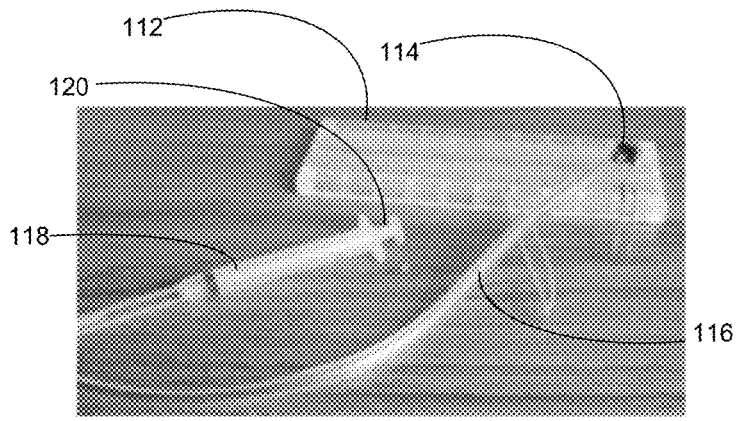
Figure 6D:
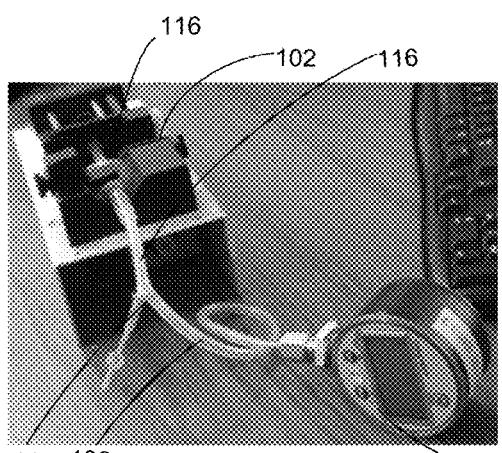
Figure 6E:
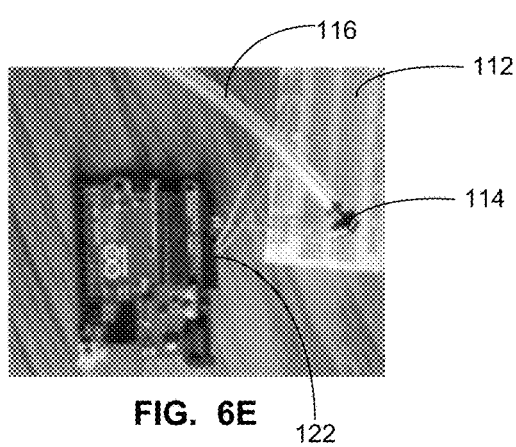

The system 100 was built using a spherical balloon 108 of a maximum inflated diameter of 10 mm (see FIG. 6B) applied over the side walls of a sharp regular medical needle (not shown) with a drilled side hole and sealed with normal bio-compatible cyanoacrylate (alternatively glue or other bonding or welding agents may be used as described previously). Other maximum inflated diameters for the spherical balloon 108 may be used depending on the geometry and stiffness of the soft material for which at least one mechanical property is being determined. The needle with the spherical balloon 108 was connected to a Y-connector 124 that was connected via tubing 116 to a syringe 118, as well as the pressure dial gage 104, shown in FIG. 6D via additional tubing 126. A pressure sensor 114 was used to measure the pressure needed to send a certain amount of fluid to the balloon 108. The pressure sensor 114 was also connected to the tubing 116 as well as a circuit board 112 via a first set of wires, as shown in FIGS. 6C and 6E. A second set of wires from the breadboard then connected the pressure sensor 114 to a micro-controller 122, which in the experiments was an Arduino Uno, although other micro-controllers may be used. The Arduino Uno 122 was coupled with the computer 106 so that the computer 106 could track the varying pressure that was measured from the pressure sensor 106 using a program (written in C-language) provided by the Arduino manufacturer.

Needle sizes of (19 G and 22 G) were used to obtain the experimental data for the prototype system 100. The inflated diameter of the balloon was usually 10 mm although in some cases the balloon 108 was inflated to a value of 12 mm diameter or greater to see the effect of the balloon 108 on the pressure reading. It was found that the pressure reading was not affected by this extra expansion of the balloon 108 and the contribution of the balloon material was found to be insignificant. In some example embodiments, it was preferable to use a needle of 22 G or smaller to make the system 100 as minimally invasive as possible.

Figure 6F:
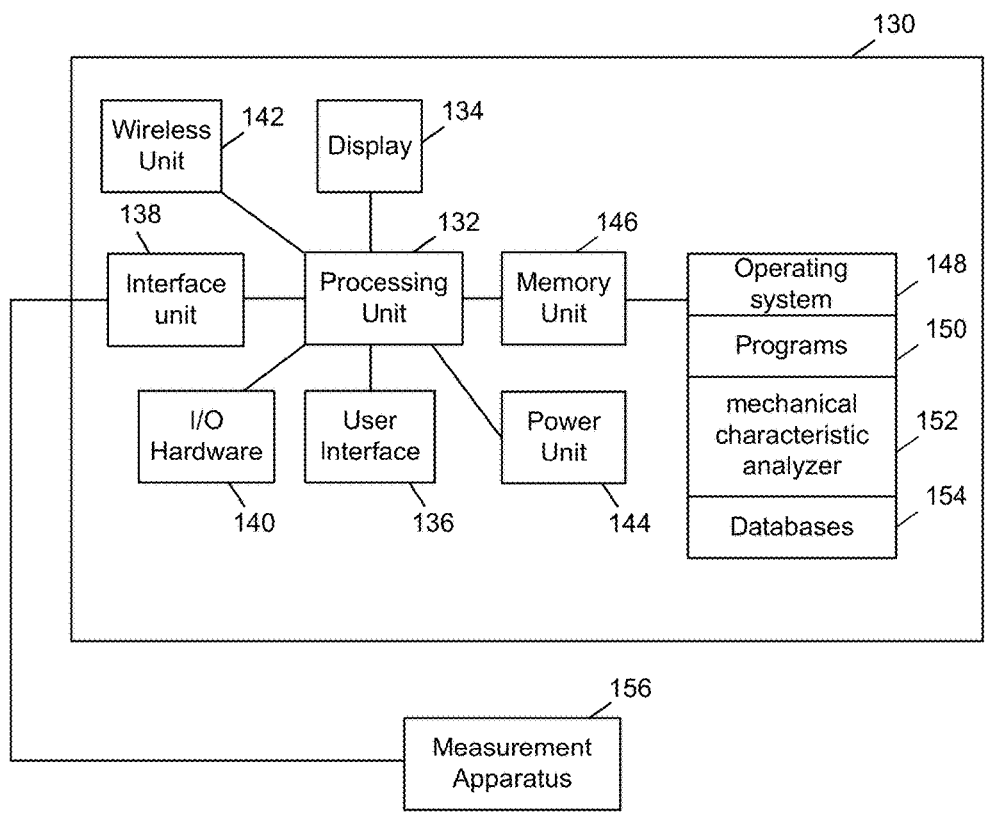

Referring now to FIG. 6F, shown therein is an example embodiment of a computing device 130 that may be used as the computer 106. The device 130 is provided as an example and there can be other embodiments of the device 130 with different components or a different configuration of the components described herein. The device 10 further includes several power supplies (not all shown) connected to various components of the device 130 for providing power thereto as is commonly known to those skilled in the art. The measurement apparatus 156 is similar to the components shown in FIGS. 1A-1C or FIGS. 6A-6E. In general, a user may interact with the computing device 130 and the measurement apparatus 156 to acquire pressure and volume data from soft material or a sample of the soft material.

The device 130 comprises a processing unit 132, a display 134, a user interface 136, an interface unit 138, Input/Output (I/O) hardware 140, a wireless unit 142, a power unit 144 and a memory unit 146. The memory unit 146 comprises software code for implementing an operating system 148, various programs 150, a mechanical characteristic analyzer 152, and one or more databases 154. Many components of the device 130 can be implemented using a desktop computer, a laptop, a mobile device, a tablet, and the like.

The processing unit 132 controls the operation of the device 130 and can be any suitable processor, controller or digital signal processor that can provide sufficient processing power depending on the configuration, purposes and requirements of the device 130 as is known by those skilled in the art. For example, the processing unit 132 may be a high performance general processor. In alternative embodiments, the processing unit 132 may include more than one processor with each processor being configured to perform different dedicated tasks. In alternative embodiments, specialized hardware can be used to provide some of the functions provided by the processing unit 132.

The display 134 can be any suitable display that provides visual information depending on the configuration of the device 130. For instance, the display 134 can be a cathode ray tube, a flat-screen monitor and the like if the device 130 is a desktop computer. In other cases, the display 134 can be a display suitable for a laptop, tablet or handheld device such as an LCD-based display and the like.

The user interface 136 can include at least one of a mouse, a keyboard, a touch screen, a thumbwheel, a track-pad, a track-ball, a card-reader, voice recognition software and the like again depending on the particular implementation of the device 130. In some cases, some of these components can be integrated with one another.

The interface unit 138 can be any interface that allows the device 10 to communicate with other devices or computers. In some cases, the interface unit 138 can include at least one of a serial port, a parallel port or a USB port that provides USB connectivity. The interface unit 138 can also include at least one of an Internet, Local Area Network (LAN), Ethernet, Firewire, modem or digital subscriber line connection. Various combinations of these elements can be incorporated within the interface unit 138.

The I/O hardware 140 is optional and can include, but is not limited to, at least one of a microphone, a speaker, a display device and a printer, for example.

The wireless unit 142 is optional and can be a radio that communicates utilizing CDMA, GSM, GPRS or Bluetooth protocol according to standards such as IEEE 802.11a, 802.11b, 802.11g, or 802.11n. The wireless unit 142 can be used by the device 130 to communicate with other devices or computers.

The power unit 144 can be any suitable power source that provides power to the device 130 such as a power adaptor or a rechargeable battery pack depending on the implementation of the device 130 as is known by those skilled in the art.

The memory unit 146 can include RAM, ROM, one or more hard drives, one or more flash drives or some other suitable data storage elements such as disk drives, etc. The memory unit 146 may be used to store an operating system 148 and programs 150 as is commonly known by those skilled in the art. For instance, the operating system 148 provides various basic operational processes for the device 130. The programs 150 include various user programs so that a user can interact with the device 130 to perform various functions such as, but not limited to, acquiring pressure and volume data from a soft material using the measurement apparatus 156, viewing and manipulating data, adjusting parameters related to data analysis as well as sending messages as the case may be.

The mechanical characteristic analyzer 152 processes the data that is recorded by the pressure and volume indicators using a mechanical relation that corresponds to the desired one or more mechanical characteristics that are being determined. The mechanical characteristic analyzer 152 is typically implemented using software, but there may be instances in which it is implemented using FPGA or application specific circuitry.

The databases 154 can be used to store data for the device 130 such as system settings, parameter values, and calibration data. The databases 154 can also store other information required for the operation of the programs 150 or the operating system 148 such as dynamically linked libraries and the like.

The device 130 comprises at least one interface that the processing unit 132 communicates with in order to receive or send information. This interface can be the user interface 136, the interface unit 138 or the wireless unit 142. For instance, measurement parameters such as the number of inflation positions, and possibly loading rate (when dealing with viscoelastic materials like tissue), may be inputted by a user through the user interface 18 or this information may be received through the interface unit 20 from a computing device. The processing unit 132 can communicate with either one of these interfaces as well as the display 134 or the I/O hardware 140 in order to output information related to the one or more determined mechanical characteristics. In addition, the device 10 can communicate information across a network connection to a remote system for storage and/or further analysis in some embodiments. This communication may also include email communication.

The device 130 may also be used to input information needed for system parameters for proper operation of the device 130 and the measurement apparatus 156 such as calibration information and other system operating parameters as is known by those skilled in the art. Data that are obtained from tests, as well as parameters used for operation of the device 130, may be stored in the memory unit 146. The stored data may include raw acquired data, preprocessed acquired data as well as processed tumor location and tumor mapping data.

Measurements Using Early Liver Samples

Experiments were performed to evaluate the sensitivity of the applicant's measurement method using two types of calf liver (i.e. regular fed and white grain fed). There is a significant difference between the stiffness of these two calf livers based on their resistance to the full expansion of the balloon inclusion. Two different soft tissue stiffness values of $6.5\times10^{-3}$ and $5.5\times10^{-3}$ MPa were obtained for the regular and white grain fed cub livers, respectively.

Figure 7A:
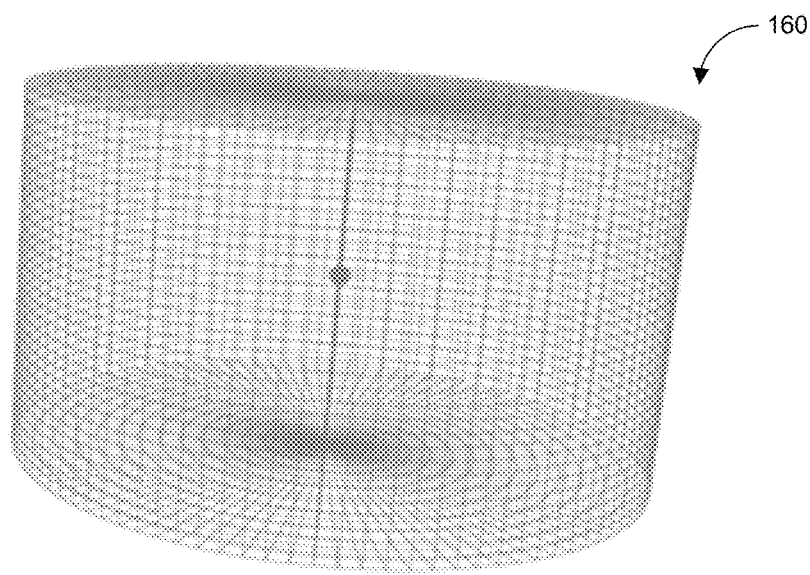
FIG. 7A is an example of a 3D finite element model for a balloon when it is surrounded by tissue.
Figure 7B:
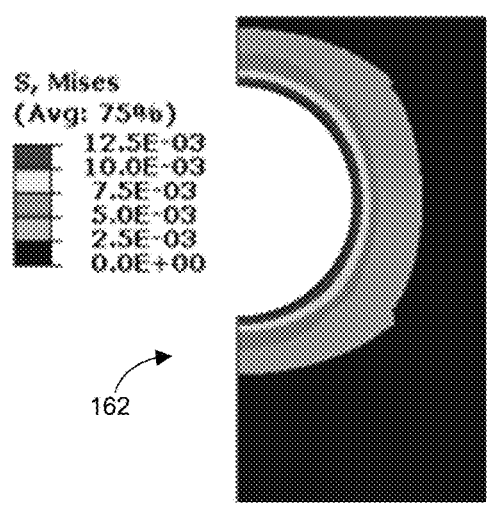
FIG. 7B is a magnified image showing the stress distribution around a fully inflated balloon from experiments on a regular fed cub liver.
Figure 7C:
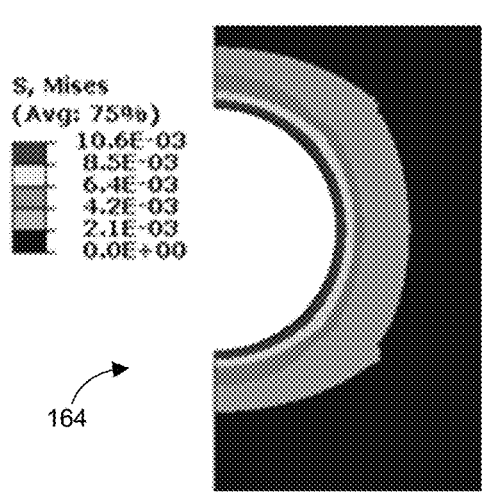
FIG. 7C is a magnified image showing the stress distribution around a fully inflated balloon from experiments on a white fed cub liver.

To further investigate these samples, a three dimensional finite element model 160 was developed to investigate the behaviour of the inflated balloon inside the soft tissues (FIG. 7A). The bubble-tissue interface was modeled using frictionless contact surfaces. This assumption was realistic given the smooth exterior surface of the balloon. The balloon was pushed radially by 5 mm from the centre (10 mm diameter) to simulate the size of the balloon (10 mm diameter) used in the experiments. Two different soft tissue stiffness values of $6.5\times10^{-3}$ and $5.5\times10^{-3}$ MPa were used to simulate the regular and white grain fed cub livers, respectively. These two values provided exactly the value of pressure applied in the experiment as shown in FIGS. 7B and 7C. In particular, FIG. 7B shows a magnified image showing the stress distribution 162 around a fully inflated balloon from experiments on a regular fed cub liver while FIG. 7C shows a magnified image showing the stress distribution 164 around a fully inflated balloon from experiments on a white fed cub liver. In addition, a number of elastic moduli reported in the literature were within 6.0 kPa (Muller et al, 2009, Lim et al. 2009) of the finite element simulation results. The analysis also showed that most of the effected region of the tissues was within a close proximity to the inflated balloon. This is an interesting feature that becomes very beneficial for localized measurement of material properties in sites with cancer, or fibrosis. This feature is important to minimize the effect of bones or large blood vessels that are close to the balloon when inflated. This was also verified in the experiments using a gel sample (see the results shown in FIGS. 8A-8C).

The stiffness values were in a good agreement with the finite element results of pressure on the internal walls of the tissue when pushed radially by 5 mm by the balloon, as illustrated in FIG. 7A. This represents a successful proof-of-principle demonstration that medically significant data can be gathered using the applicant's measurement method.

Measurements on Gel and Liver Samples

Figure 8A:
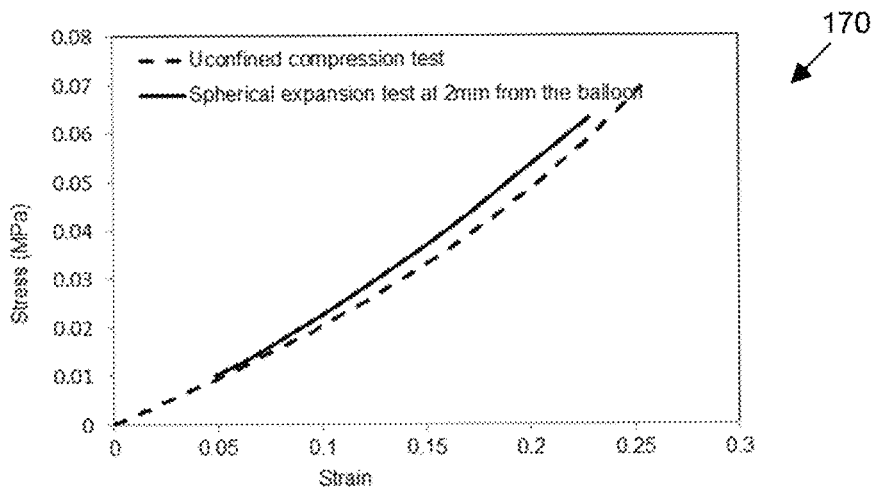
FIGS. 8A to 8C are graphs showing a comparison between the stress-strain relationships of an unconfined compression test and the measurement methods taught herein at different distances from the balloon surface inside surrounding material including at 2 mm from the contact surface, 3 mm from the contact surface, and 5 mm from the contact surface, respectively.
Figure 8B:
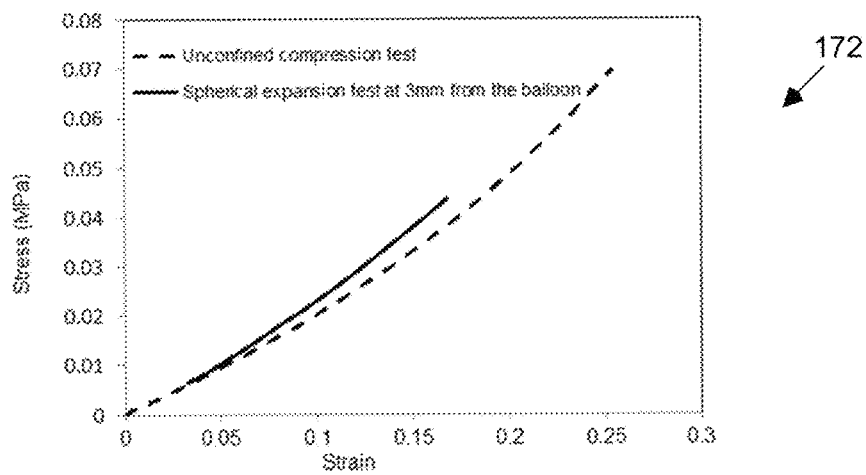
Figure 8C:
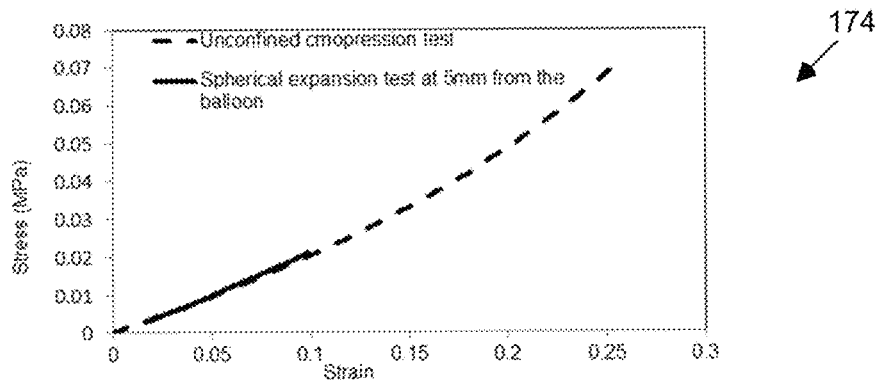

Different gels with different degrees of softness (due to different manufacturing processes for these different gels) were investigated using the applicant's measurement method and the results were compared to conventional unconfined compression tests. The results of both methods were in a good agreement using the general approach explained earlier in the section entitled "Conventional compressible and linear elastic materials". FIGS. 8A-8C shows the stress-strain curves of a gel sample using balloon expansion at different distances from the bubble-gel interface and the unconfined pressure test. In particular, FIG. 8A-8C shows test results at 2 mm from the contact surface, 3 mm from the contact surface, and 5 mm from the contact surface, respectively.

Using the simplified method at strain levels of <0.25 strain (just enough strain to avoid tissue rupture), fresh samples of animal liver were collected from a local butchers shop and tested under different volume changes of the balloon to determine the pressure-volume relationship. These liver samples were investigated using the applicant's measurement method and tensile testing. Once again, the results using both methods are in good agreement where the modulus of elasticity was determined to be 26 kPa and 27 kPa using the applicant's measurement method and the tensile test, respectively.

Measurements Showing Effect of Balloon that is a Non-Perfect Sphere

Figure 9:
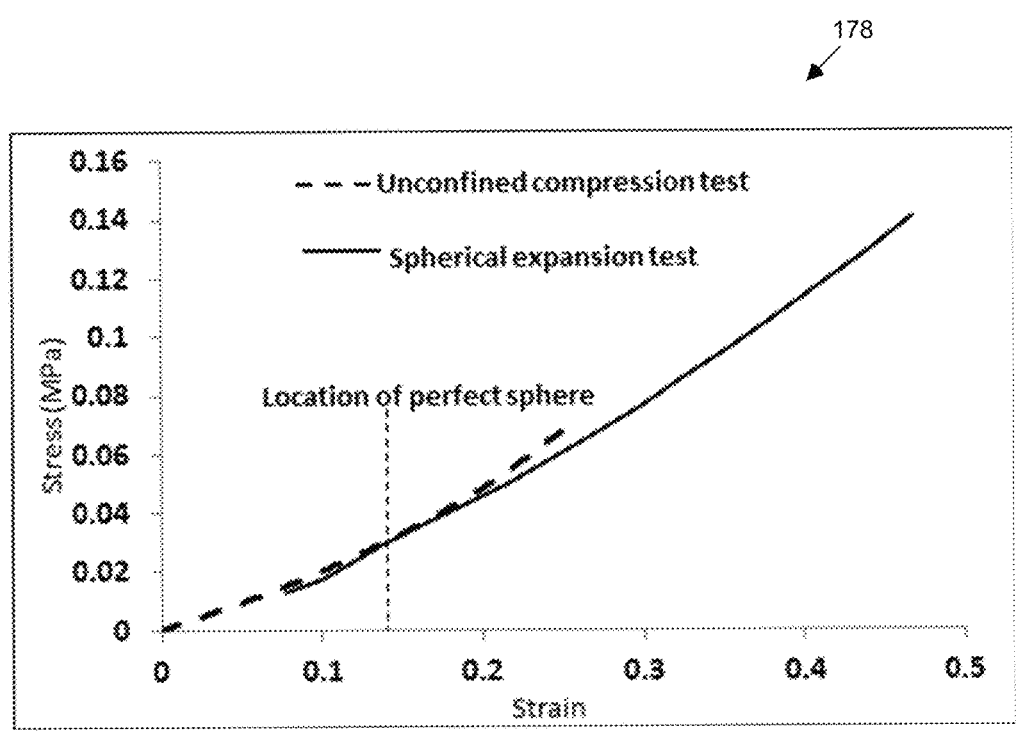
FIG. 9 is a graph showing experimental results of the effect that a balloon that deviates from a perfect sphere has on the measurement analysis described herein.

Referring now to FIG. 9, shown therein is a graph 178 showing experimental results of the effect that a balloon that deviates from a perfect sphere has on the measurement analysis described herein. The phrase "deviation from a perfect sphere" means that the balloon was not inflated fully (for a diameter less than 10 mm) or it was extra inflated to a larger than 10 mm diameter. One of results shown in the graph is from an unconfined compression test where a gel was placed under direct compression while stress and strain (i.e. a change in length/original length) were monitored. In particular, a polyvinyl alcohol (PVA) hydrogel was placed between two smooth plates (one plate on top of the gel and the other plate on the bottom of the gel) and a regular Instron loading machine (Instron model 4465) was used to apply the compression. The other curve shows the results of the sphere expansion measurement method in which a balloon was inserted into the same gel material and inflated while measurements were made. The balloon was 10 mm in diameter and 0.2 mm thick and it was attached to a 22 G needle (around 0.7 mm diameter).

Figure 10:
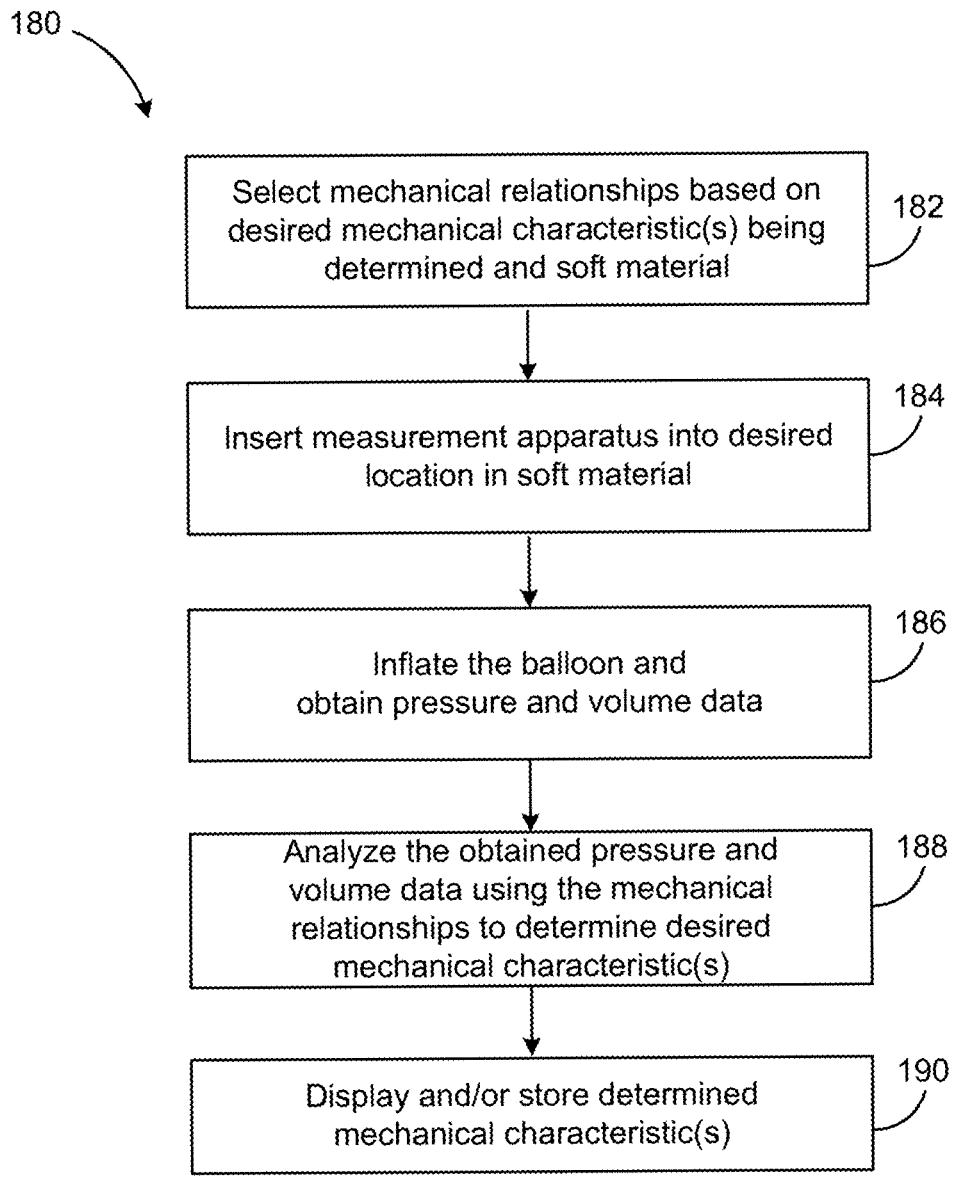
FIG. 10 shows a flowchart of an example embodiment of a measurement method for measuring at least one mechanical property of a soft material in accordance with the teachings herein.

Referring now to FIG. 10, shown therein is a flowchart of an example embodiment of a measurement method 180 for measuring one or more desired mechanical properties or characteristics of soft material. At 182 of the measurement method 180, the one or more mechanical characteristics of the soft material that will be measured are chosen and then the mechanical relationships are selected that will be used on measured data to measure the desired mechanical characteristic(s). The desired mechanical characteristic(s) may vary depending on the type of soft material as well as the application in which the soft material is being used. Likewise, the mechanical relationships that will be used will vary depending on the desired mechanical characteristic(s) being measured.

The measurement method 180 then proceeds to act 184 at which point the measurement apparatus is inserted into the soft material at a desired location with the balloon in the deflated position. The desired location most likely depends on the type of soft material, such as when the soft material is homogeneous in which case the desired location may be various locations or when the soft material is heterogeneous such as a region within an organ where the region may be a tumor.

The method 180 then proceeds to act 186 once the measurement apparatus is inserted at the desired location. At 186, the balloon is inflated by introducing fluid into the balloon. While the balloon is being inflated, a set of pressure and volume measurement data points are obtained in which the pressure that is required to insert a certain volume of fluid into the balloon is determined. For example, in some cases it may be sufficient to obtain only one volume and pressure data point to determine a desired mechanical characteristic of the soft tissue while other mechanical characteristics are determined using a set of volume and corresponding pressure data points. For time dependent mechanical characteristics such as relaxation properties, a certain volume of fluid is injected and kept constant for a period of time while pressure points required to keep the volume constant are collected over the time period. On other hand, for creep properties measurement, the volume changes required to maintain a constant pressure is monitored. Once the pressure and volume data is obtained, the fluid can be removed from the balloon so that it transitions to the deflated position and can be removed from the soft material.

Once the pressure and volume data is obtained, the method moves to act 184 at which point the mechanical relationships selected at act 188 may then be used along with the pressure and volume data to determine values for the one or more desired mechanical characteristics. The mechanical relationship may comprise starting with a pressure-volume relationship and then converting the pressure-volume relationship to another mechanical relationship for the desired mechanical characteristic(s) such as, but not limited to, a stress-stretch relationship, a stress-strain relationship or a modulus of elasticity.

For example, in some cases, the full stress-strain curve is used to characterize the soft material (i.e. multiple stress-strain points are needed which means multiple volume and pressure data points are obtained). However, in other cases, only one stress-strain point may need to be measured as the slope of the line between this specific point and the zero-zero point may be the mechanical characteristic which is being characterized (e.g. this slope represents the modulus of elasticity). The pressure-volume data and stress-strain relationship can be used to calculate other mechanical properties including, but not limited to, the bulk modulus (i.e. ratio of pressure to volume change), shear modulus, material resilience (e.g. the material's ability to absorb energy within the elastic deformation range), and viscoelastic properties (e.g. time dependent, parameters such creep and relaxation parameters), for example. Table 1 provides examples of different mechanical characteristics that may be measured for certain types of soft tissue and the type of measured data that may be used.

TABLE 1

| Mechanical Characteristics | Pressure-Volume data required | Example of material application |
| --- | --- | --- |
| Full stress strain curve | Full pressure-volume data | All soft materials (e.g.: gels and rubber-like silicon, soft tissues (e.g.: liver and lungs, etc.)) |
| Material resilience | Full pressure-volume data | All soft materials (e.g.: gels and rubber-like silicon, soft tissues (e.g.: liver and lungs, etc.)) |
| Modulus of elasticity | Segment of pressure-volume data (or one point) | Depending on the required details of the analysis (e.g.: all soft materials like gels and rubber-like silicon and soft tissues (e.g.: liver, and lungs, etc.)) |
| Bulk modulus | Segment of pressure-volume data (or one point) | Depending on the required details of the analysis (e.g.: all soft materials like gels and rubber-like silicon, and soft tissues (e.g.: liver and lungs, etc.)) |
| Shear modulus | Segment of pressure-volume data (or one point) | Depending on the required details of the analysis (e.g.: soft tissues, gels, and rubber-like silicon) |
| Viscoelastic properties | One data point of pressure with multiple volume data points over a period of time for creep. OR One data point of volume with multiple pressure data points over a period of time for relaxation. | All soft materials (e.g.: gels, rubber-like silicon, and soft tissues (examples: liver and lungs, etc.) |

At 190, the determined mechanical characteristic(s) may then be displayed or stored in a data store. The determined mechanical characteristic(s) may be displayed on a monitor of a computing device or printed on paper. Alternatively, the determined mechanical characteristic(s) may be transmitted to another computing device where it is used in a certain application.

For example, in one aspect, the determined mechanical characteristic(s) of the soft material may be used in biomechanical based deformable image registration using finite element modeling for various medical procedures including, but not limited to, image guided radiotherapy, image guided surgery, and brachytherapy, for example.

In another aspect, the determined mechanical characteristic(s) of the soft material may be used as a diagnostic tool. For example, liver fibrosis and cancer tumors are much stiffer than normal healthy tissue. Accordingly, in some embodiments, a difference in stiffness determined using the methods taught herein may be used with thresholds determined from normal tissue and abnormal tissue (having tumors or fibrosis) populations to detect or predict cancer occurrence. For example, a dense breast is likely to develop cancer than softer one.

It should be noted that in some embodiments the measurement method 180 may be used on data that is already obtained. Therefore, in these cases, the method 180 does not use acts 184 and 186.

It should be noted that in an alternative embodiment, the desired mechanical characteristic(s) are continuously determined in real time as they are used in applications which require the desired mechanical characteristic(s) to be monitored for a period of time and possibly used as an input which may have a physical effect. For example, for advanced biomechanical modeling that is used in radiotherapy and surgery applications, time dependent parameters are needed. One example of this is image guided surgery. Cutting tissues during surgery may result in relaxing the tissues. Since the tissue material properties are not linear, relaxing the tissue through cutting means shifting the pressure-volume data point from an upper portion of the stress-strain curve to a lower portion of the stress-strain curve. This means that the Region of Interest (ROI) that the surgeon is targeting will move to another spatial coordinate not similar to that based on the initial pressure-volume data (before the surgical cut). Performing the measurements in real-time is important so that the surgeon accurately performs the surgery. For example, the deformation due to tissue relaxation can be determined using a patient-specific image-based finite element model that uses the mechanical property measured in real-time based on the teachings herein and the change in deformation can be provided to the surgeon to provide guidance for further surgical cuts during surgery.

In addition, organs (such as lungs) during breathing impose different levels of compression between an inhale cycle and an exhale cycle. Similar to the previous surgery example, a radiotherapist has to change the location of a radiation beam that is directed to a patient during radiation treatment based on the characteristics of the patient's lungs under pressure since the treatment location will change due to the compression.

In addition, certain tissues may behave differently when they are imaged to determine a treatment region and when the tissue is actually treated due to the position of a patient. For example, in breast cancer, an oncologist may rely on a mammogram or MRI imaging to locate and treat a breast tumor yet these images are taken when the breast is compressed (e.g. mammogram) or under its own gravity loading (e.g. the patient is lying face down during MRI). However, the treatment is applied frequently when the patient is sleeping on their back (e.g. face up) in which case one or more mechanical properties of the breast will change and the treatment location will change so a real-time mechanical characterization of the soft tissue can be used to ensure that the treatment is delivered to the proper region.

In another example application, in radiotherapy, the abdomen can be compressed using an external plate to minimize the movement of the liver during breathing. In some cases, the pressure is relaxed after a period of time. The abdomen will relax due to the viscoelastic characteristics of the soft tissues in that organ. In fact, a few minutes after the start of the compression by the external plate, the abdominal tissue relaxes so a real-time mechanical characterization of the soft tissue can be used to again ensure that the treatment is delivered to the proper region.

It should also be understood that at least some of the elements described herein that are at least partially implemented via software may be written in a high-level procedural language such as object oriented programming or a scripting language. Accordingly, the program code may be written in at least one of C, C++, SQL or any other suitable programming language and may comprise modules or classes, as is known to those skilled in object oriented programming. It should also be understood that at least some of the elements of the microcircuitry that are implemented via software may be written in at least one of assembly language, machine language or firmware as needed. In either case, the program code can be stored on a storage media or on a computer readable medium that bears computer usable instructions for one or more processors and is readable by a general or special purpose programmable computing device having at least one processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

Furthermore, the computer readable medium may be provided in various non-transitory forms such as, but not limited to, one or more diskettes, compact disks, tapes, chips, USB keys, magnetic and electronic storage media and external hard drives, and in some cases in various transitory forms such as, but not limited to, wire-line transmissions, satellite transmissions, internet transmissions or downloads, digital and analog signals, and the like. The computer useable instructions may also be in various forms, including compiled and non-compiled code.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments described herein, the general scope of which is defined in the appended claims.

REFERENCES

Borisov, A. V. (2010), "Elastic analysis of multilayered thick-walled spheres under external load", MECHANIKA, No. 4(84), pp. 28-32.
Boyce, M. C. and Arruda, E. M. 2000. Constitutive Models of Rubber Elasticity: A Review. Rubber chemistry and technology 73: pp. 504-523.
Fung, Y. C. (1993) "Biomechanics: Mechanical Properties of Living Tissues", Springer-Verlag, New York, second edition.
Gent, A. N.; and Lindley P. B. (1959), "Internal Rupture of Bonded Rubber Cylinders in Tension", Proceedings of The Royal Society A: Mathematical, Physical and Engineering Sciences, vol. 249, no. 1257, pp. 195-205.
Lim, Y. J.; Deo, D., Singh, T. P., Jones, D. B, De, S. (2009) "In situ measurement and modeling of biomechanical response of human cadaveric soft tissues for physics-based surgical simulation", Surgical endoscopy 23, pp. 1298-1307.
Kerdok, A. E., Ottensmeyer, M. P., and Howe, R. D. (2006) "Effects of perfusion on the viscoelastic characteristics of liver", Journal of Biomechanics 39, pp. 2221-2231.
Martins, P. A. L. S., Natal Jorge, R. M., and Ferreira A. J. M. (2006). A Comparative Study of Several Material Models for Prediction of Hyperelastic Properties: Application to Silicone-Rubber and Soft Tissues. Strain 42: pp. 135-147.
Miller, K. (2005) "Method of testing very soft biological tissues in compression", Journal of Biomechanics 38, pp. 153-158.
Misra, K., Ramesh, T., and Okamura A. M. (2008) "Modeling of tool tissue interactions for computer-based surgical simulation: A literature review", Presence-Teleoperators and Virtual Environments 17 pp. 463-491.
Muller, M., Gennisson, J. L., Deffieux, T., Tenter, M., and Fink, M. (2009) "Quantitative viscoelasticity mapping of human liver using supersonic shear imaging: preliminary in vivo feasibility study", Ultrasound in Medicine and Biology 35, pp. 219-229.
Roylance, David (2001); "Engineering Viscoelasticity", http://ocw.mit.edu/courses/materials-science-and-engineering/3-11-mechanics-of-materials-fall-1999/modules/visco.pdf

The invention claimed is:

1. A measurement system for measuring at least one mechanical property of a region of interest of a soft material, the measurement system comprising:
    a balloon that is disposed within the region of interest of the soft material, the balloon being inflatable from a deflated position to at least one inflated position during use to provide volume data;
    a volume indicator to measure the volume data for the balloon at each inflated position;
    a pressure indicator to measure pressure data for a corresponding pressure needed to inflate the balloon to each inflated position; and
    a mechanical characteristic analyzer that is configured to determine a pressure-volume relationship based on the measured volume and pressure data to capture an expansion resistance of the soft material around the balloon, translate the pressure-volume relationship into a mechanical relationship that corresponds to the at least one mechanical property and use the mechanical relationship to determine the at least one mechanical property.

2. The measurement system of claim 1, further comprising:
    a fluid reservoir for containing a fluid that is used to inflate the balloon;
    a conduit that is coupled to the fluid reservoir and the balloon; and
    an actuator that is coupled to the fluid reservoir to apply a force to drive the fluid from the fluid reservoir to the balloon via the conduit to inflate the balloon during use.

3. The measurement system of claim 2, wherein the conduit comprises at least one aperture that is in fluid communication with the balloon and the balloon is attached and has edges sealed circumferentially around the conduit using one of bio-compatible cyanoacrylate, a glue, a bonding agent or a welding agent.

4. The measurement system of claim 2, wherein the fluid comprises a liquid or a gas.

5. The measurement system of claim 2, wherein the fluid comprises distilled water.

6. The measurement system of claim 2, further comprising tubing to couple the conduit with the fluid reservoir, the fluid reservoir is a syringe and the conduit is a needle.

7. The measurement system of claim 6, wherein the actuator comprises a syringe pump and the pressure indicator is a pressure sensor.

8. The measurement system of claim 6, wherein the soft material comprises organic tissue and the needle comprises a 19 G, 20 G, 22 G or 26 G needle.

9. The measurement system of claim 2, wherein the soft material comprises organic tissue and the balloon has a thickness that ranges from 0.02 to 0.05 mm and inflated diameters for different inflation positions including 3, 5 and 10 mm.

10. The measurement system of claim 1, wherein the soft material comprises tissue.

11. The measurement system of claim 1, wherein the mechanical relationship comprises a stress-stretch relationship or a stress-strain relationship.

12. The measurement system of claim 1, wherein the soft material comprises a rubber-like material and the mechanical relationship comprises one of a neo-Hookean, a Mooney-Rivlin, a polynomial Rivlin, a Yeoh, an Arruda and Boyce, and an Ogden strain energy function.

13. The measurement system of claim 1, wherein the mechanical relationship relates a modulus of elasticity of the soft material to the volume and pressure data.

14. A method of measuring at least one mechanical property of a region of interest of a soft material, the method comprising:
    inserting a balloon in a deflated position within the region of interest;
    inflating the balloon to at least one inflated position;
    measuring volume and pressure data comprising a volume of the balloon at each inflated position and a corresponding pressure used to inflate the balloon to each inflated position; and
    determining a pressure-volume relationship based on the measured volume and pressure data to capture an expansion resistance of the soft material around the balloon, translating the pressure-volume relationship into a mechanical relationship that corresponds to the at least one mechanical property and using the mechanical relationship to determine the at least one mechanical property.

15. The method of claim 14, further comprising inserting a fluid into the balloon to inflate the balloon.

16. The method of claim 15, further comprising inserting a gas or a liquid into the balloon to inflate the balloon.

17. The method of claim 15, wherein a pump is used to insert the fluid into the balloon and the measured volume is obtained from a flow rate of the pump.

18. The method of claim 15, wherein using the mechanical relationship to determine the at least one mechanical property comprises using a stress-stretch relationship, a stress-strain relationship or a modulus of elasticity as the mechanical relationship.

19. The method of claim 15, wherein the soft material comprises a rubber-like material and the determining act comprising using one of a neo-Hookean strain, a Mooney-Rivlin, a polynomial Rivlin, a Yeoh, an Arruda and Boyce, and an Ogden energy function as the mechanical relationship.

* * * * *